US010179768B2

(12) United States Patent
Aiken et al.

(10) Patent No.: US 10,179,768 B2
(45) Date of Patent: *Jan. 15, 2019

(54) ELECTROCHROMIC TWO-CORE VIOLOGEN DERIVATIVES AND OPTICAL ARTICLES CONTAINING THEM

(71) Applicant: ESSILOR INTERNATIONAL (COMPAGNIE GENERALE D'OPTIQUE), Charenton-le-Pont (FR)

(72) Inventors: Stuart Aiken, York (GB); Daniel Luke Crossley, Normanton West Yorkshire (GB); Christopher David Gabbutt, Preston (GB); Bernard Mark Heron, Brough (GB); Claudine Biver, Charenton-le-Pont (FR); Samuel Archambeau, Charenton-le-Pont (FR); Fabien Berit-Debat, Charenton-le-Pont (FR)

(73) Assignee: ESSILOR INTERNATIONAL, Charenton-le-Pont (FR)

(*) Notice: Subject to any disclaimer, the term of this patent is extended or adjusted under 35 U.S.C. 154(b) by 6 days.

This patent is subject to a terminal disclaimer.

(21) Appl. No.: 15/022,841

(22) PCT Filed: Sep. 16, 2014

(86) PCT No.: PCT/EP2014/069734
§ 371 (c)(1),
(2) Date: Mar. 17, 2016

(87) PCT Pub. No.: WO2015/040031
PCT Pub. Date: Mar. 26, 2015

(65) Prior Publication Data
US 2016/0221949 A1 Aug. 4, 2016

(30) Foreign Application Priority Data
Sep. 17, 2013 (EP) .................... 13184780

(51) Int. Cl.
C07D 213/06 (2006.01)
C07D 213/22 (2006.01)
C07D 213/80 (2006.01)
C07D 213/26 (2006.01)
C09K 9/02 (2006.01)
C07D 213/803 (2006.01)
G02C 7/10 (2006.01)
G02F 1/15 (2006.01)

(52) U.S. Cl.
CPC ......... C07D 213/22 (2013.01); C07D 213/06 (2013.01); C07D 213/26 (2013.01); C07D 213/80 (2013.01); C07D 213/803 (2013.01); C09K 9/02 (2013.01); G02C 7/101 (2013.01); G02F 1/1521 (2013.01); C09K 2211/1029 (2013.01); G02F 2001/1515 (2013.01)

(58) Field of Classification Search
CPC ..................................... C07D 213/06
USPC ........................................... 546/257
See application file for complete search history.

(56) References Cited

U.S. PATENT DOCUMENTS

| 4,116,535 | A | 9/1978 | Ponjee et al. ................. 359/272 |
|---|---|---|---|
| 5,278,693 | A | 1/1994 | Theiste et al. ................ 359/272 |
| 5,438,024 | A | 8/1995 | Bolton et al. .................... 501/55 |
| 5,998,617 | A | 12/1999 | Srinivasa et al. ............. 544/347 |
| 6,141,137 | A | 10/2000 | Byker et al. .................. 359/265 |
| 6,255,238 | B1 | 7/2001 | Brocheton ...................... 501/56 |
| 7,106,489 | B2 | 9/2006 | Berneth et al. ............... 359/273 |
| 8,736,946 | B2 | 5/2014 | Archambeau et al. ....... 359/275 |
| 9,823,534 | B2* | 11/2017 | Aiken ................... G02F 1/1521 |
| 2002/0027700 | A1 | 3/2002 | Berneth et al. ............... 359/265 |
| 2005/0231784 | A1 | 10/2005 | Shinohara et al. ........... 359/265 |
| 2009/0082570 | A1 | 3/2009 | Nii et al. ....................... 546/258 |
| 2011/0235150 | A1 | 9/2011 | Das et al. ..................... 539/273 |

FOREIGN PATENT DOCUMENTS

| EP | 0180204 | 5/1986 |
|---|---|---|
| EP | 1156098 | 11/2001 |
| EP | 2407526 | 1/2012 |
| EP | 2848667 | 3/2015 |
| EP | 2848668 | 3/2015 |
| FR | 2937154 | 4/2010 |
| FR | 2950710 | 4/2011 |
| GB | 1514466 | 6/1978 |
| JP | S52135884 | 11/1977 |
| JP | S5437080 A | 3/1979 |
| JP | H11106376 | 4/1999 |
| WO | WO 1998/044384 | 10/1998 |

(Continued)

OTHER PUBLICATIONS

Database CA [Online] Chemical Abstracts Service, Columbus, Ohio, US; 1982 "Composition for electrochromic displays", XP002724222, retrieved from STN Database accession No. 1982:605815 abstract-& JP 57 057779 A (Mitsubishi Electric Corp., Japan) Apr. 7, 1982 (Apr. 7, 1982).

Database CA [Online] Chemical Abstracts Service, Columbus, Ohio, US; 1980, "Electrochromic substances for display devices", XP002724143, retrieved from STN Database accession No. 1980:613419 abstract—& JP 55 054381 A (Hitachi, Ltd., Japan) Apr. 21, 1980 (Apr. 21, 1980).

Clennan et al., "Pyrylogens: Synthesis, Structural, Electrochemical, and Photophysical Characterization of a New Class of Electron Transfer Sensitizers", *J Am Chem Soc*, 130(24): 7552-3, 2008.

(Continued)

Primary Examiner — Patricia L Morris
(74) Attorney, Agent, or Firm — Norton Rose Fulbright US LLP

(57) ABSTRACT

The present invention relates to a group of novel electrochromic materials. More specifically, it relates to electrochromic materials having two-core viologens and the use of these two-core viologens as a variable transmittance medium for the manufacture of an optical article, such as an ophthalmic lens.

5 Claims, No Drawings

(56) References Cited

FOREIGN PATENT DOCUMENTS

| WO | WO 2006/013250 | 2/2006 |
| WO | WO 2008/028930 | 3/2008 |
| WO | WO 2010/024840 | 3/2010 |
| WO | WO 2011/082354 | 7/2011 |
| WO | WO 2015/040029 | 3/2015 |
| WO | WO 2015/040030 | 3/2015 |
| WO | WO 2015/040033 | 3/2015 |

OTHER PUBLICATIONS

Downes, "Aryl-substituted Derivatives of 4,4'-Bipyridylium Salts: their Spectroscopic Properties and Stereochemistry", *J. Chem. Soc. (C)*, p. 1491-93, 1967.
International Search Report and Written Opinion issued in PCT/EP2014/069731, dated Apr. 10, 2015.
International Search Report and Written Opinion issued in PCT/EP2014/069737, dated Apr. 15, 2015.
International Search Report and Written Opinion issued in PCT/EP2014/069730, dated Apr. 15, 2015.
International Search Report and Written Opinion issued in PCT/EP2014/069734, dated Oct. 6, 2014.

\* cited by examiner

ELECTROCHROMIC TWO-CORE VIOLOGEN DERIVATIVES AND OPTICAL ARTICLES CONTAINING THEM

CROSS-REFERENCE TO RELATED APPLICATIONS

This application is a national phase application under 35 U.S.C. § 371 of International Application No. PCT/EP2014/069734 filed 16 Sep. 2014, which claims priority to European Patent Application No. 13184780.8 filed 17 Sep. 2013. The entire contents of each of the abovereferenced disclosures is specifically incorporated by reference herein without disclaimer.

The present invention relates to a group of novel electrochromic materials. More specifically, it relates to electrochromic materials having two-core viologens and the use of these two-core viologens as a variable transmittance medium for the manufacture of an optical article, such as an ophthalmic lens.

Electrochromism is a well-known physical phenomenon which is observed with certain classes of chemical compounds that change reversibly colour when a voltage is applied to them. The material undergoes reversible changes in optical properties by oxidation and reduction. Usually the electrochromic material may be colourless when an electric field is not applied and may be coloured when an electric field is applied. An electrochromic device, i.e. a device containing electrochromic compounds, the visible light absorbance of which depends only on the presence of an electric field, can thus have two states, i.e. a coloured state (when electrically activated) and a bleached state (in the inactive state). The optical transmission properties of the device depend on the nature of the electrochromic compounds.

There remains a need for improving an electrochromic material in order to use them as transparent media for forming high quality optical articles, in particular high quality ophthalmic lenses, while keeping electrochromic properties and having a wide range of colours.

After conducting extensive research, the present inventors provide novel electrochromic compounds exhibiting not only good electrochromic properties such as high absorption of the visible light in the coloured state, fast colouring and fading rates, long-term stability but also can be incorporated easily in a cell to form for instance an electrochromic lens.

The applicants now have synthesized a group of novel electrochromic two-core viologens.

The present invention relates to electrochromic compounds of formula (I) as defined below.

The present invention also relates to an electrochromic composition comprising at least one compound of formula (I).

Finally, the present invention relates to an electrochromic device comprising said electrochromic composition, such as ophthalmic lens.

Thus, the present invention concerns electrochromic compounds represented by formula (I):

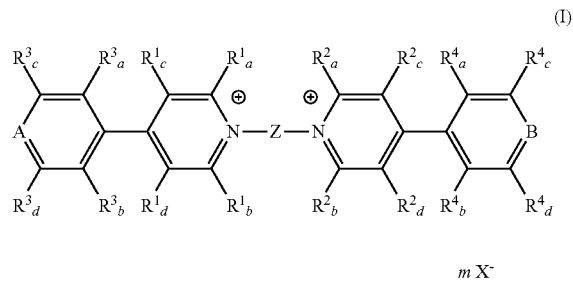

wherein:
Z is selected from:
  alkylene;
  cycloalkylene; and
  a bivalent group of formula —$R^5$—Y—$R^6$—, wherein
    $R^5$ and $R^6$ are each independently selected from single bond, alkylene and cycloalkylene, and
    Y is selected from arylene, cycloalkylene, heteroarylene, arylene-arylene or arylene-CR'R"-arylene wherein R' and R" form together with the carbon to which they are linked a carbocyclic group;
  wherein said alkylene, cycloalkylene, arylene, heteroarylene, and carbocyclic groups may be substituted by one or more substituents selected from halogen, alkyl, alkoxy, alkylthio, hydroxyalkyl, acyloxy, cycloalkyl, aryl, substituted aryl, aryloxy, heteroaryl and substituted heteroaryl;
A and B are respectively selected from nitrogen and —$N^+(R^{7a})$—, and from nitrogen and —$N^+(R^{7b})$—, wherein $R^{7a}$ and $R^{7b}$ are independently selected from:
  alkyl which may be substituted by one or more groups independently selected from halogen, alkoxy, cycloalkyl, vinyl, allyl, aryl, substituted aryl, heteroaryl and substituted heteroaryl;
  aryl and heteroaryl which may be both substituted by one or more groups independently selected from:
    halogen, cyano, nitro, alkyl, haloalkyl, arylalkyl, cycloalkyl, cycloalkylalkyl and heterocycloalkylalkyl, alkenyl, alkynyl, allyl, vinyl, aryl, substituted aryl, heteroaryl, substituted heteroaryl, —N(aryl)$_2$-, —N(aryl)CO(aryl), —CO— aryl and —CO-substituted aryl;
    —OR$^8$, —SR$^8$, —S(O)R$^8$, —S(O$_2$)R$^8$, —S(O$_2$)NR$^8$R$^9$, —NR$^8$R$^9$, —NR$^8$COR$^9$, —NR$^8$CO(aryl), —NR$^8$aryl, —CH$_2$OR$^8$, —CH$_2$SR$^8$, —CH$_2$R$^8$, —CO—R$^8$ and —CO$_2$R$^8$ wherein R$^8$ and R$^9$ are independently selected from H, alkyl, haloalkyl, arylalkyl, cycloalkyl, cycloalkylalkyl and heterocycloalkylalkyl;
    —S(O$_2$)NR$^{10}$R$^{11}$ and —NR$^{10}$R$^{11}$, wherein R$^{10}$ and R$^{11}$ form together with the nitrogen atom to which they are linked a saturated 5 to 7 membered heterocycloalkyl which may comprise in addition to the nitrogen atom one further heteroatom selected from oxygen, nitrogen and sulfur, and which may be optionally substituted by one or two groups independently selected from halogen, —R$^8$, —OR$^9$, and —NR$^8$R$^9$, wherein R$^8$ and R$^9$ are as defined above;
    —V—W—R$^{12}$ wherein:
      V is selected from oxygen, —N(R$^8$)—, sulfur, —S(O)— and —S(O$_2$)— wherein R$^8$ is as defined above;

W is alkylene, which may be substituted by one or more groups independently selected from halogen and alkoxy; and $R^{12}$ is selected from —$OR^8$, —$NR^8$(alkyl) and —$SR^8$ wherein $R^8$ is as defined above; and —OC(O)—$R^{13}$ wherein $R^{13}$ is selected from alkyl, haloalkyl, alkenyl, —W—$R^{12}$, and aryl group which may be substituted by 1 to 4 groups selected from halogen, —$R^8$, —$OR^8$, —$SR^8$, —$NR^8R^9$, —$NR^{10}R^{11}$, —CO—$R^8$, —C(O)$OR^8$ wherein $R^8$, $R^9$, $R^{10}$, $R^{11}$, $R^{12}$ and W are as defined above.

$R^1{}_a$, $R^1{}_b$, $R^1{}_c$, $R^1{}_d$, $R^2{}_a$, $R^2{}_b$, $R^2{}_c$, $R^2{}_d$, $R^3{}_a$, $R^3{}_b$, $R^3{}_c$, $R^3{}_d$, $R^4{}_a$, $R^4{}_b$, $R^4{}_c$ and $R^4{}_d$ are each independently selected from H, alkyl, alkoxy, alkylthio, haloalkyl, haloalkoxy, haloalkylthio, poly(alkylenoxy), alkoxycarbonyl, aryl, substituted aryl, heteroaryl and substituted heteroaryl, wherein the alkyl group may be substituted by one or more substituents independently selected from alkoxy, cycloalkyl, aryl, substituted aryl, heteroaryl and substituted heteroaryl;

wherein at least one of $R^1{}_a$, $R^1{}_b$, $R^1{}_c$, $R^1{}_d$, $R^2{}_a$, $R^2{}_b$, $R^2{}_c$, $R^2{}_d$, $R^3{}_a$, $R^3{}_b$, $R^3{}_c$, $R^3{}_d$, $R^4{}_a$, $R^4{}_b$, $R^4{}_c$ and $R^4{}_d$ is not H;

$X^-$ is a counterion; and m is 2 if A and B are nitrogen, 3 if one of A and B is nitrogen and the other is not nitrogen, and 4 if both A and B are not nitrogen.

The expression "alkylene" represents any divalent radical of a linear or branched hydrocarbon chain comprising 1 to 12 carbon atoms. Examples of $C_1$-$C_{12}$ alkylene groups include $C_1$-$C_4$ alkylene groups such as —$CH_2$—, —$(CH_2)_2$—, —$(CH_2)_3$—, —$(CH_2)_4$—, —CH($CH_3$)—, —CH($CH_3$)—$CH_2$—, —$CH_2$—CH($CH_3$)—, —$(CH_2)_2$CH($CH_3$)—, —$CH_2$—CH($CH_3$)—$CH_2$— or —CH($CH_3$)—$(CH_2)_2$—, as well as —$(CH_2)_5$—, —$(CH_2)_6$—, —$(CH_2)_2$CH($CH_3$)—$(CH_2)_2$—, —$(CH_2)_3$—CH($CH_3$)—$CH_2$—, —$(CH_2)_7$—, —$(CH_2)_8$—, —$(CH_2)_9$—, —$(CH_2)_{10}$—, —$(CH_2)_{11}$—, —$(CH_2)_{12}$—.

The expression "cycloalkylene" represents any divalent radical of a monocyclic or bicyclic 3 to 12 membered carbocycle. Examples of $C_3$-$C_{12}$ alkylene groups include cyclopropylene, cyclopentylene, cyclohexylene, cycloheptylene, and decahydronaphthylene.

The expression "arylene" represents any divalent radical of an aromatic hydrocarbon comprising 6 to 18 carbon atoms. Examples of $C_6$-$C_{18}$ arylene groups include phenylene, naphthylene, anthracenylene and phenanthrenylene.

The expression "carbocyclic group" represents any monocyclic or fused polycyclic hydrocarbon rings comprising 3 to 20 carbon atoms and which may comprise one or more unsaturations. Examples of $C_3$-$C_{20}$ carbocyclic groups include $C_{10}$-$C_{20}$ fused hydrocarbon rings which may comprise one or more unsaturations, such as cyclohexenylene, indene, fluorene.

The expression "halogen" includes F, Cl, Br or I. Preferred halogens are F and Cl.

The expression "alkyl" represents any monovalent radical of a linear or branched hydrocarbon chain comprising 1 to 18 carbon atoms. Examples of $C_1$-$C_{18}$ alkyl groups include $C_1$-$C_4$ alkyl groups such as methyl, ethyl, n-propyl, i-propyl, n-butyl, i-butyl, s-butyl or t-butyl, $C_6$-$C_8$ alkyl groups such as n-hexyl, n-heptyl or n-octyl, as well as n-pentyl, 2-ethylhexyl, 3,5,5-trimethylhexyl, n-nonyl, n-decyl, n-undecyl, n-dodecyl or n-Octadecyl.

The expression "alkenyl" represents any monovalent radical of a linear or branched hydrocarbon chain from 2 to 18 carbon atoms and comprising one double bound. Examples of $C_2$-$C_{12}$ alkenyl groups include $C_2$-$C_4$ alkenyl groups such as ethenyl, n-propenyl, i-propenyl, n-butenyl or i-butenyl.

The expression "alkynyl" represents any monovalent radical of a linear or branched hydrocarbon chain from 2 to 12 carbon atoms and comprising one triple bound which may be either internal or terminal. Examples of $C_2$-$C_{12}$ alkynyl groups include $C_2$-$C_4$ alkynyl groups such as ethynyl, n-propynyl, n-butynyl.

The expression "alkoxy" represents a radical of formula —OR wherein R is a $C_1$-$C_{12}$ alkyl. Examples of $C_1$-$C_{12}$ alkoxy groups include $C_1$-$C_6$ alkoxy groups such as —$OCH_3$, —$OCH_2CH_3$ or $O(CH_2)_5CH_3$.

The expression "cycloalkyl" represents any monovalent radical of a monocyclic or bicyclic 3 to 12 membered saturated carbocycle. Examples of $C_3$-$C_{12}$ cycloalkyl groups include cyclopropyl, cyclopentyl and cyclohexyl.

The expression "heterocycloalkyl" represents any monovalent radical of a monocyclic or bicyclic 3 to 12 membered saturated ring comprising one or two heteroatoms independently selected from oxygen, nitrogen and sulfur. Examples of $C_3$-$C_{12}$ heterocycloalkyl groups include for example tetrahydropyranyl or N-methylpiperidinyl.

The expression "cycloalkylalkyl" represents any ($C_3$-$C_{12}$ cycloalkyl)-substituted $C_1$-$C_{12}$ alkyl group. Examples of ($C_3$-$C_{12}$ cycloalkyl)-$C_1$-$C_{12}$ alkyl groups include ($C_3$-$C_{12}$ cycloalkyl)-$C_1$-$C_4$ such as cyclohexylmethyl or cyclohexylethyl.

The expression "heterocycloalkylalkyl" represents any ($C_3$-$C_{12}$ heterocycloalkyl)-substituted $C_1$-$C_{12}$ alkyl group. Examples of ($C_3$-$C_{12}$ heterocycloalkyl)-$C_1$-$C_{12}$ alkyl groups include ($C_3$-$C_{12}$ heterocycloalkyl)-$C_1$-$C_4$ such as tetrahydropyranylmethyl.

The expression "aryl" represents any monovalent radical of an aromatic hydrocarbon comprising 6 to 18 carbon atoms. Examples of $C_6$-$C_{18}$ aryl groups include phenyl and naphthyl, anthacenyl, phenanthrenyl.

The expression "substituted aryl" represents any $C_6$-$C_{18}$ aryl group as defined above substituted by one or more substituents selected from halogen, alkyl, alkoxy, haloalkyl, haloalkoxy, alkoxycarbonyl, alkanoyl, aroyl, formyl, nitrile, nitro, amido, alkylthio, alkylsulfinyl, alkylsulfonyl, arylthio, arylsulfinyl, arylsulfonyl, amino, alkylamino, arylamino, dialkylamino and diarylamino. Preferably, the substituents are selected from bulky or electron withdrawing groups. Examples of substituted $C_6$-$C_{18}$ aryl groups include substituted phenyl groups such as p-methylphenyl, o-t-butylphenyl, p-trifluoromethoxyphenyl, o-trifluoromethoxyphenyl, m-cyanophenyl, o-i-propylphenyl, 2,4-dinitrophenyl, 2,6-diisopropylphenyl or 3,5-dicyanophenyl.

The expression "aryloxy" represents a radical of formula —OR wherein R is a $C_6$-$C_{18}$ aryl. Examples of $C_1$-$C_{12}$ aryloxy groups include phenyloxy and naphthyloxy.

The expression "heteroaryl" represents any monovalent radical of a monocyclic or bicyclic 5 to 10 membered aromatic group comprising from 1 to 3 heteroatoms independently selected from oxygen, nitrogen and sulfur. Examples of $C_5$-$C_{10}$ heteroaryl groups include furyl, thienyl, pyrrolyl, pyrazoyl, imidazolyl, isoxazolyl, isothiazoyl, thiazolyl, oxazolyl, 1,2,3-triazolyl, 1,2,4-triazolyl, 1-benzofuryl, 1-benzothienyl, indolyl, benzimidazolyl, indazolyl, 1,2-benzisoxazolyl, 2,1-benzisoxazolyl 1,2-benzisothiazolyl, 2,1-benzisothiazolyl benzothiazolyl, benzoxazolyl, benzotriazolyl, pyridyl, quinolinyl, isoquinolinyl, pyridazinyl, cinnolinyl, phthalazinyl, pyrimidinyl, quinazolinyl, pyrazinyl and quinoxalinyl.

The expression "heteroarylene" represents any divalent radical of a monocyclic or bicyclic 5 to 10 membered aromatic group comprising from 1 to 3 heteroatoms independently selected from oxygen, nitrogen and sulfur. Examples of $C_5$-$C_{10}$ heteroarylene groups include furylene, thienylene, pyrrolylene, pyrazoylene, imidazolylene, isoxazolylene, isothiazolylene, thiazolylene, oxazolylene, 1,2,3-triazolylene, 1,2,4-triazolylene, 1-benzofurylene, 1-benzothienylene, indolylene, benzimidazolylene, indazolylene, 1,2-benzisoxazolylene, 2,1-benzisoxazolylene, 1,2-benzisothiazolylene, 2,1-benzisothiazolylene, benzothiazolylene, benzoxazolylene, benzotriazolylene, pyridylene, quinolinylene, isoquinolinylene, pyridazinylene, cinnolinylene, phthalazinylene, pyrimidinylene, quinazolinylene, pyrazinylene and quinoxalinylene.

The expression "substituted heteroaryl" represents any $C_5$-$C_{10}$ heteroaryl group as defined above substituted by one or more substituents selected from alkyl, alkoxy, alkoxycarbonyl, alkanoyl, aroyl, formyl, nitrile, nitro, amido, alkylthio, alkylsulfinyl, alkylsulfonyl, arylthio, arylsulfinyl, arylsulfonyl, amino, alkylamino, arylamino, dialkylamino and diarylamino. Preferably, the substituents are selected from bulky or electron withdrawing groups. Examples of substituted $C_5$-$C_{10}$ heteroaryl groups include 4-methylthienyl, 5-methyl-2-thienyl, 6-methyl-2-pyridyl, N-methylpyrrol-2-yl and N-phenylindol-3-yl.

The expression "haloalkyl" represents any $C_1$-$C_{12}$ alkyl group substituted by one or more halogen atom such as F or Cl. Examples of $C_1$-$C_{12}$ haloalkyl groups include $C_1$-$C_{12}$ perhaloalkyl groups, in particular $C_1$-$C_4$ perhaloalkyl groups such as —$CF_3$, as well as $C_1$-$C_{12}$ (perhaloalkyl)alkyl groups, in particular ($C_1$-$C_4$ perhaloalkyl)-($C_1$-$C_4$ alkyl) groups such as —$CH_2CF_3$.

The expression "haloalkoxy" represents a radical of formula —OR wherein R is a $C_1$-$C_{12}$ haloalkyl. Examples of $C_1$-$C_{12}$ haloalkoxy groups include $C_1$-$C_{12}$ perhaloalkoxy groups, in particular $C_1$-$C_4$ perhaloalkoxy groups such as —$OCF_3$, as well as $C_1$-$C_{12}$ (perhaloalkyl)alkoxy groups, in particular ($C_1$-$C_4$ perhaloalkyl)-($C_1$-$C_4$ alkoxy) groups such as —$OCH_2CF_3$.

The expression "alkylthio" represents a radical of formula —SR wherein R is a $C_1$-$C_{12}$ alkyl. Examples of $C_1$-$C_{12}$ alkylthio groups include —$SCH_3$ and —$SCH_2CH_3$.

The expression "haloalkylthio" represents a radical of formula —SR wherein R is a $C_1$-$C_{12}$ haloalkyl. Examples of $C_1$-$C_{12}$ haloalkoxy groups include $C_1$-$C_{12}$ perhaloalkylthio groups, in particular $C_1$-$C_4$ perhaloalkylthio groups such as —$SCF_3$, as well as $C_1$-$C_{12}$ (perhaloalkyl)alkylthio groups, in particular ($C_1$-$C_4$ perhaloalkyl)-($C_1$-$C_4$ alkylthio) groups such as —$SCH_2CF_3$.

The expression "hydroxyalkyl" represents any $C_1$-$C_{12}$ alkyl group substituted by one or more hydroxyl groups. Examples of $C_1$-$C_{12}$ hydroxyalkyl groups include —$CH_2OH$ and —$CH_2CH_2OH$.

The expression "acyloxy" represents a radical of formula —OC(O)R wherein R is a $C_1$-$C_{12}$ alkyl. Examples of $C_1$-$C_{12}$ acyloxy groups include —$OC(O)CH_3$ and —$OC(O)CH_2CH_3$.

The expression "polyalkylenoxy" represents a radical of formula —O(R'O)$_m$R wherein R' is a $C_1$-$C_{12}$ alkylene, R is a $C_1$-$C_{12}$ alkyl and m is an integer from 1 to 12. Examples of poly($C_1$-$C_{12}$ alkylenoxy) groups include $OCH_2CH_2OMe$.

The expression "alkoxycarbonyl" represent a radical of formula —C(O)OR wherein R is a $C_1$-$C_{18}$ alkyl. Examples of $C_1$-$C_{18}$ alkoxycarbonyl groups include $C_1$-$C_4$ alkoxycarbonyl groups such as —$C(O)OCH_3$ and —$C(O)OC_2H_5$.

In formula (I), Z, called "the central core", is preferably selected from $C_1$-$C_{12}$ alkylene, $C_3$-$C_7$ cycloalkylene, $C_3$-$C_{14}$ arylene, $C_5$-$C_{10}$ heteroarylene, ($C_1$-$C_4$ alkylene)-($C_3$-$C_{14}$ arylene), ($C_1$-$C_4$ alkylene)-($C_3$-$C_{14}$ heteroarylene), ($C_1$-$C_4$ alkylene)-($C_3$-$C_{14}$ arylene)-($C_1$-$C_4$ alkylene), ($C_1$-$C_4$ alkylene)-($C_3$-$C_{14}$ heteroarylene)-($C_1$-$C_4$ alkylene), ($C_3$-$C_{14}$ arylene)-($C_3$-$C_{14}$ arylene), ($C_1$-$C_4$ alkylene)-($C_3$-$C_{14}$ arylene)-($C_3$-$C_{14}$ arylene)-($C_1$-$C_4$ alkylene) and ($C_3$-$C_{14}$ arylene)-(CR'R")—($C_3$-$C_{14}$ arylene) wherein R' and R" form together with the carbon to which they are linked a $C_3$-$C_{20}$ carbocyclic group; wherein the arylene and cycloalkylene groups may be substituted by one or more substituents selected from halogen, $C_1$-$C_4$ alkyl, $C_1$-$C_4$ alkoxy and $C_3$-$C_7$ cycloalkyl, and the alkylene groups may be substituted by one or more substituents selected from halogen, $C_3$-$C_{14}$ alkyl, $C_1$-$C_{12}$ alkoxy, $C_2$-$C_{12}$ acyloxy, $C_1$-$C_{12}$ hydroxyalkyl, $C_3$-$C_{12}$ cycloalkyl, phenyl phenyloxy and substituted phenyl. In particular, substituted alkylene include —$CH_2$(CR$^a$R$^b$)$CH_2$— wherein R$^a$ and R$^b$ may be independently selected from H, $C_3$-$C_{14}$ alkyl, $C_3$-$C_{12}$ cycloalkyl, (cycloalkyl)methyl, aryl, substituted aryl, arylalkyl such as benzyl or phenyl($C_2$-$C_7$ alkyl), phenyloxyethyl, substituted arylalkyl, $C_1$-$C_{12}$ alkoxy, $C_2$-$C_{12}$ acyloxy, $C_1$-$C_{12}$ hydroxyalkyl, and $C_1$-$C_{12}$ alkoxymethyl.

More preferably, Z is selected from $C_1$-$C_{12}$ alkylene, aryl substituted $C_1$-$C_{12}$ alkylene, phenylene, naphthylene, ($C_1$-$C_4$ alkylene)-phenylene-($C_1$-$C_4$ alkylene), ($C_1$-$C_4$ alkylene)-naphthylene-($C_1$-$C_4$ alkylene) such as naphthylene bis(methylene), quinoxaline-2,3-diyl, ($C_1$-$C_4$ alkylene)-quinoxaline-2,3-diyl-($C_1$-$C_4$ alkylene) such as quinoxaline-2,3-diylbis(methylene), phenylene-phenylene, ($C_1$-$C_4$ alkylene)-phenylene-phenylene-($C_1$-$C_4$ alkylene) and phenylene-fluorenylene-phenylene. For example, Z may be selected from —$CH_2$—, —$(CH_2)_2$—, —$(CH_2)_3$—, —$(CH_2)_4$—, —$(CH_2)_5$—, —$CH_2$—$CH(CH_3)$—$CH_2$—, —$CH_2$—$CH(CH_2Phenyl)$—$CH_2$—, —$(CH_2)_2$—$CH(CH_3)$—$CH_2$—, —$(CH_2)_3$—$CH(CH_3)$—$CH_2$—, —$(CH_2)_2$—$CH(CH_3)$—$(CH_2)_2$—,

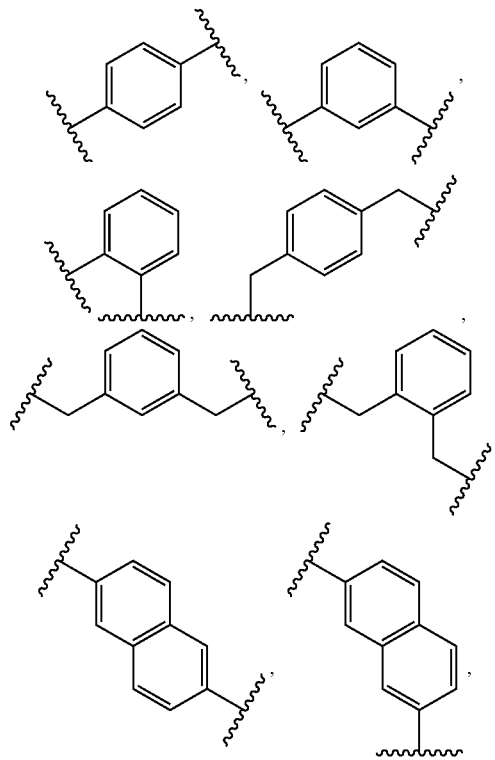

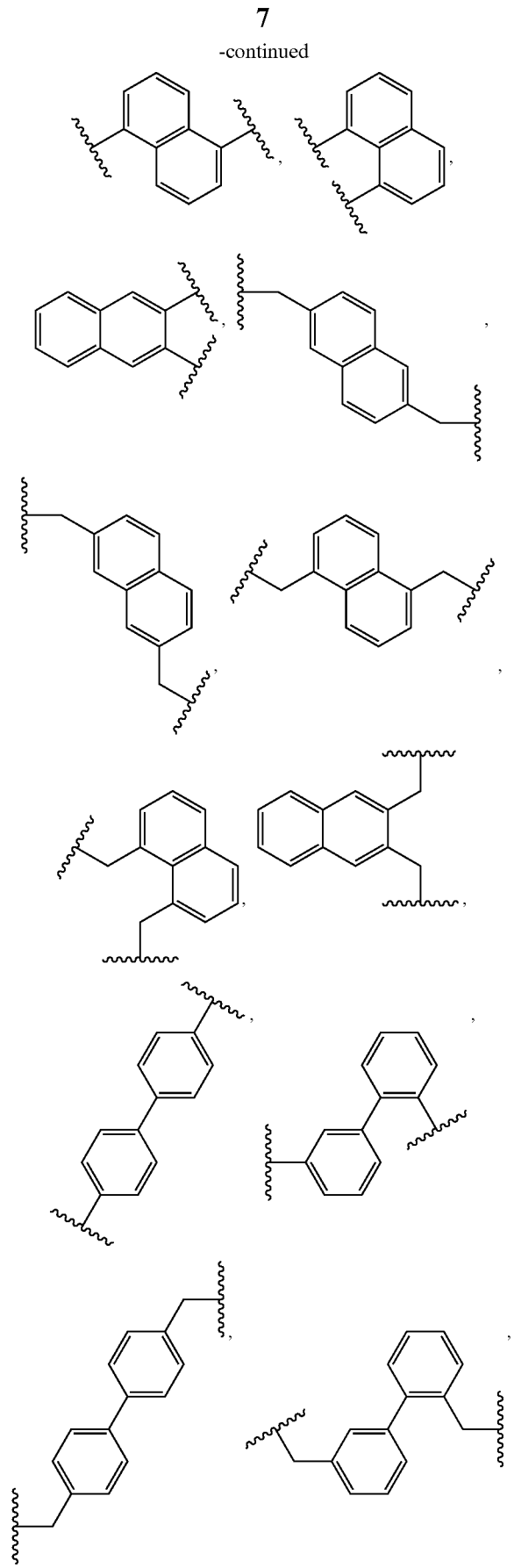

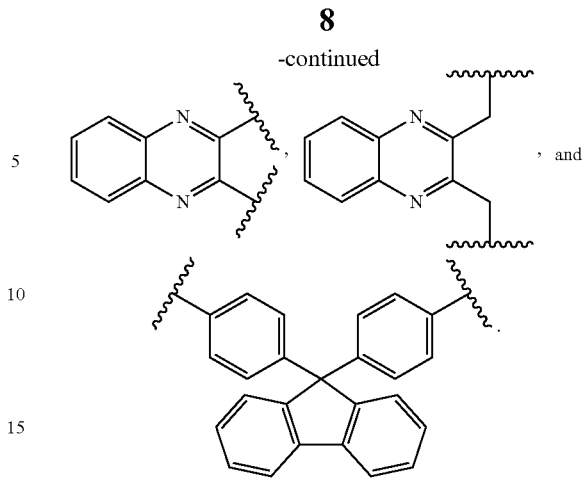

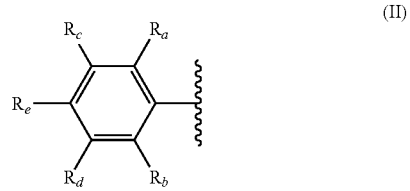

A and B are preferably respectively selected from nitrogen and —N⁺(R$^{7a}$)—, and from nitrogen and —N⁺(R$^{7b}$)—, wherein R$^{7a}$ and R$^{7b}$ are independently selected from $C_6$-$C_8$ alkyl, in particular n-hexyl, and phenyl or naphthyl, wherein phenyl and naphthyl may be both substituted by one or more substituents independently selected from halogen, cyano, nitro, hydroxy, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, $C_3$-$C_7$ cycloalkyl, ($C_3$-$C_7$ cycloalkyl)$C_1$-$C_4$ alkyl.

In particular, A and B may be selected from —N($C_6$-$C_8$ alkyl)-, preferably —N⁺($C_6H_{13}$)—, more preferably —N⁺(n-$C_6H_{13}$)—, which have a good solubility in conventional solvents used in electrochromic compositions such as propylene carbonate while maintaining a fast fading rate to the bleached state. Indeed, $C_1$-$C_5$ alkyl substituted viologen compounds are more difficult to solubilise in some solvents used in electrochromic compositions like some ionic liquids. On the contrary, higher alkyl substituted two-core viologen compounds have good solubility. However, when two-core viologen compounds are substituted with long chain alkyls having more than 8 carbon atoms the fading rate tends to decrease, which prevents a fast reversibility to the bleached state.

Also, the inventors have observed that the presence of aryl substituents, in particular phenyl substituents, on the viologen cores of compounds of the present invention results in the stabilization of the compounds of the invention and, consequently, in a decrease of the activation potential, which corresponds to an increase in the reduction potential, of the viologen compounds. Therefore, in a preferred embodiment, A and B may be respectively selected from nitrogen and —N⁺(R$^{7a}$)—, and from nitrogen and —N⁺(R$^{7b}$)—, wherein R$^{7a}$ and R$^{7b}$ are independently selected from optionally substituted phenyl groups represented by formula (II):

(II)

$$\begin{array}{c} R_c \quad\quad R_a \\ R_e \quad\quad \\ R_d \quad\quad R_b \end{array}$$

wherein $R_a$, $R_b$, $R_c$, $R_d$ and $R_e$ are each independently selected from H, halogen, cyano, nitro, hydroxyl, alkyl, benzyl, haloalkyl, alkoxy, alkylthio, haloalkoxy, acyl, aroyl, alkoxycarbonyl, cycloalkyl, allyl, aryl and heteroaryl. In a particular embodiment, at least one of $R_a$, $R_b$, $R_c$, $R_d$ and $R_e$ is not H. Preferably, at least one of $R_a$, $R_b$, $R_c$, $R_d$ and $R_e$ is selected from halogen, cyano, nitro, hydroxyl, haloalkyl, haloalkoxy, alkoxycarbonyl, aryl and heteroaryl. Indeed, the applicant found that such electron-withdrawing substituents stabilize the cation which results in a decrease of the activation potential. In a preferred embodiment, $R_e$ is H and at least one of $R_a$, $R_b$, $R_c$ and $R_d$ is not H.

For example, at least one of $R_a$, $R_b$, $R_c$, $R_d$ and $R_e$ may be selected from methyl, i-propyl, t-butyl, cyano, trifluoromethoxy preferably trifluoromethoxy. Thus, A and B may be respectively —N$^+$(R$^{7a}$)— and —N$^+$(R$^{7b}$)—, wherein R$^{7a}$ or R$^{7b}$ are independently selected from:

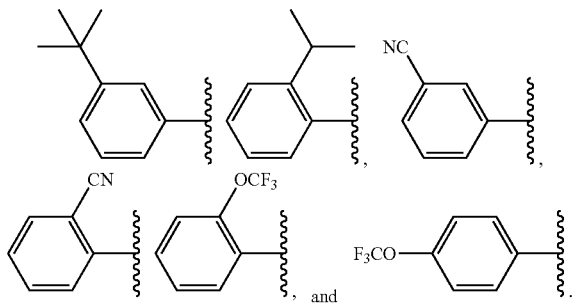

In a preferred embodiment, A and B are respectively —N$^+$(R$^{7a}$)— and —N$^+$(R$^{7b}$)—, wherein R$^{7a}$ or R$^{7b}$ are respectively selected from substituted phenyl groups of formula (II), wherein $R_c$, $R_d$ and $R_e$ are H and $R_a$ and $R_b$ are as defined above provided that at least one of $R_a$ and $R_b$ is not H. In particular, A and B are independently selected from —N$^+$(R$^{7a}$)— and —N$^+$(R$^{7b}$)— wherein R$^{7a}$ or R$^{7b}$ may be selected from:

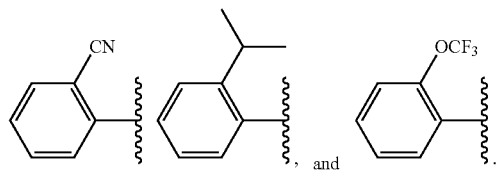

Indeed, the Applicant has found that the presence of a substituent in the ortho position of the phenyl group results in a hypsochromic effect compared to the meta position, which provides itself a hypsochromic effect compared to the para position. Indeed the maximum wavelength $\lambda_{max}$ in the absorption spectrum for a similar compound is higher when the substituent is in the para position of the phenyl group, than in the meta position, and a fortiori than in the ortho position. Consequently, the present invention provides new electrochromic compounds that can have a wide range of colours in their coloured state, in particular in the low visible wavelength—i.e. blue couloured state—, while presenting good stability and close oxydo-reduction potential values to each other.

The counterion X$^-$ may be any anion that maintains electric neutrality of the viologen compounds of formula (I). X$^-$ is preferably selected from halide, preferably fluoride and chloride, tetrafluoroborate, tetraphenylborate, perchlorate, hexafluorophosphate, nitrate, methanesulfonate, trifluoromethane sulfonate, toluene sulfonate, hexachloroantimonate, bis(trifluoromethanesulfonyl)imide, acetate and sulfate.

Preferably, $R^1_a$, $R^1_b$, $R^1_c$, $R^1_d$, $R^2_a$, $R^2_b$, $R^2_c$, $R^2_d$, $R^3_a$, $R^3_b$, $R^3_c$, $R^3_d$, $R^4_a$, $R^4_b$, $R^4_c$ and $R^4_d$ are each independently selected from hydrogen, aryl, substituted aryl, heteroaryl and substituted heteroaryl, preferably selected from optionally substituted phenyl, more preferably selected from phenyl, tolyl and cumyl.

In a first embodiment, the present invention relates to compounds of formula (I-1):

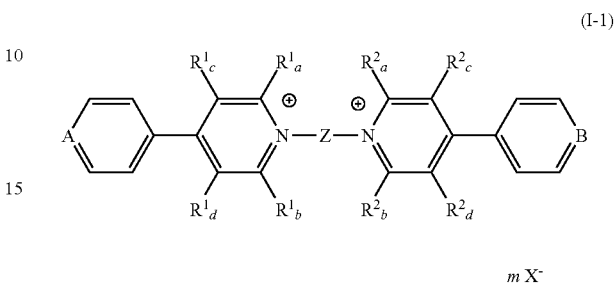

(I-1)

$m$ X$^-$ wherein Z, A, B, $R^1_a$, $R^1_b$, $R^1_c$, $R^1_d$, $R^2_a$, $R^2_b$, $R^2_c$, $R^2_d$, X$^-$ and m are as defined above.

$R^1_a$, $R^1_b$, $R^1_c$, $R^1_d$, $R^2_a$, $R^2_b$, $R^2_c$ and $R^2_d$ are preferably selected from H, aryl, substituted aryl, heteroaryl and substituted heteroaryl provided that at least one of $R^1_a$, $R^1_b$, $R^1_c$, $R^1_d$, $R^2_a$, $R^2_b$, $R^2_c$ and $R^2_d$ is not H.

Indeed, aryl, heteroaryl, substituted aryl and substituted heteroaryl are particularly preferred, more particularly optionally substituted phenyl such as phenyl, tolyl and cumyl, because they induce a decrease of the activation potential of the compounds of the invention. Moreover, the steric hindrance provided by the presence of such substituents on the viologen cores of the compounds of the invention is believed to prevent π-π interactions between the aromatic viologen cores which is the cause of the stacking phenomenon on or near the electrode surface. For example, $R^1_a$, $R^1_b$, $R^1_c$, $R^1_d$, $R^2_a$, $R^2_b$, $R^2_c$ and $R^2_d$ may be selected from H, aryl and heteroaryl, wherein the aryl and heteroaryl may be substituted by one or more substituents selected from $C_1$-$C_4$ alkyl and $C_1$-$C_4$ haloalkyl, wherein at least one of $R^1_a$, $R^1_b$, $R^1_c$, $R^1_d$, $R^2_a$, $R^2_b$, $R^2_c$ and $R^2_d$ is not H.

Particularly preferred compounds are compounds of formula (I-3):

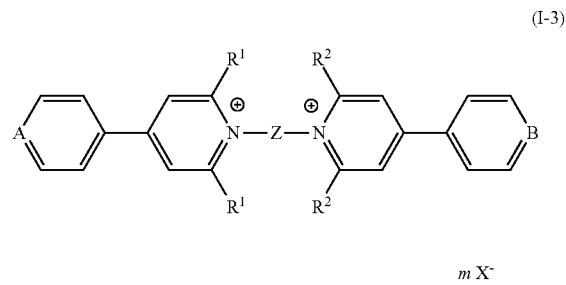

(I-3)

$m$ X$^-$ wherein Z, A, B, X$^-$ and m are as defined above and R$^1$ and R$^2$ are each independently selected from H, alkyl, alkoxy, alkylthio, haloalkyl, haloalkoxy, haloalkythio, polyalkylenoxy, alkoxycarbonyl, aryl, substituted aryl, heteroaryl and substituted heteroaryl, wherein the alkyl group may be substituted by one or more substituents independently selected from alkoxy, cycloalkyl, aryl, substituted aryl, heteroaryl and substituted heteroaryl, provided that at least one of R$^1$ and R$^2$ is not H; preferably, none of R$^1$ and R$^2$ is H; more preferably, R$^1$ and R$^2$ are independently selected from aryl, heteroaryl, substituted aryl and substituted heteroaryl. For example, R$^1$ and R$^2$, may be independently selected from phenyl, p-methylphenyl and p-trifluoromethylphenyl. In a particular embodiment, R$^1$ and R$^2$ are identical.

In a second embodiment, the present invention relates to compounds of formula (I-4):

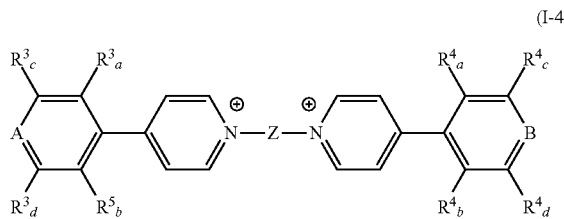

(I-4)

$m\ X^-$ wherein Z, A, B, $R^3_a$, $R^3_b$, $R^3_c$, $R^3_d$, $R^4_a$, $R^4_b$, $R^4_c$, $R^4_d$, X and m are as defined above.

$R^3_a$, $R^3_b$, $R^3_c$, $R^3_d$, $R^4_a$, $R^4_b$, $R^4_c$ and $R^4_d$ are preferably each independently selected from H, $C_1$-$C_4$ alkyl and $C_1$-$C_4$ alkoxycarbonyl, provided that at least one of $R^3_a$, $R^3_b$, $R^3_c$, $R^3_d$, $R^4_a$, $R^4_b$, $R^4_c$ and $R^4_d$ is not H. For example, $R^3_a$, $R^3_b$, $R^3_c$, $R^3_d$, $R^4_a$, $R^4_b$, $R^4_c$ and $R^4_d$ may be independently selected from methyl and ethoxycarbonyl. In a particular embodiment, none of $R^3_a$, $R^3_b$, $R^3_c$, $R^3_d$, $R^4_a$, $R^4_b$, $R^4_c$ and $R^4_d$ is H.

In a particularly preferred embodiment, the compounds of the present invention are selected from the group consisting of:

| Compound | Formula |
| --- | --- |
| 1-1 | (structure with Ph groups, 2BF$_4^\ominus$) |
| 1-2 | (structure with Ph groups, 2BF$_4^\ominus$) |
| 1-3 | (structure with n-C$_6$H$_{13}$ and Ph groups, 4BF$_4^\ominus$) |
| 1-4 | (structure with n-C$_6$H$_{13}$ and Ph groups, 4BF$_4^\ominus$) |
| 1-5 | (structure with Tol and Me groups, 2 BF$_4^\ominus$) |

-continued
| Compound | Formula |
|---|---|
| 1-6 | 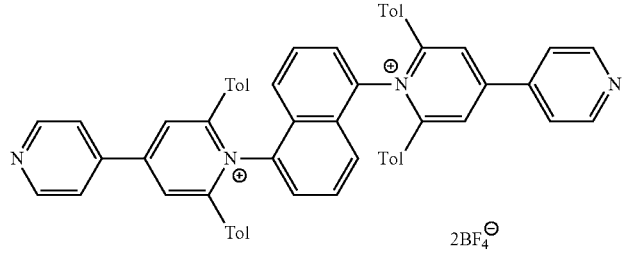 2BF$_4^\ominus$ |
| 1-7 | 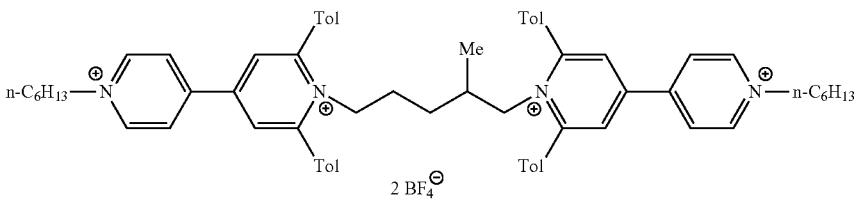 2 BF$_4^\ominus$ |
| 1-8 | 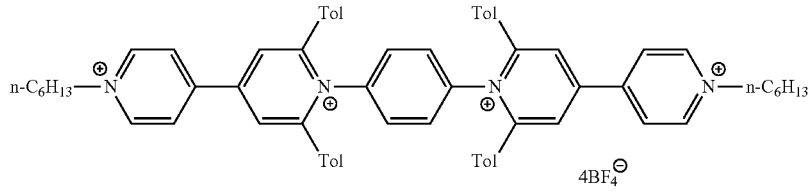 4BF$_4^\ominus$ |
| 1-9 | 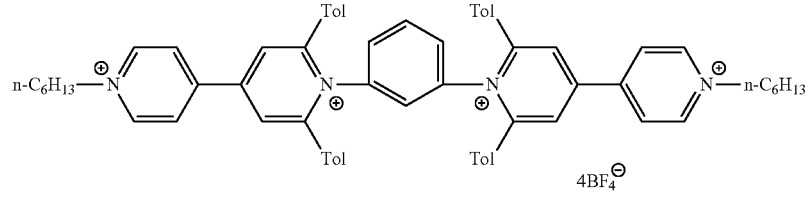 4BF$_4^\ominus$ |
| 1-10 | 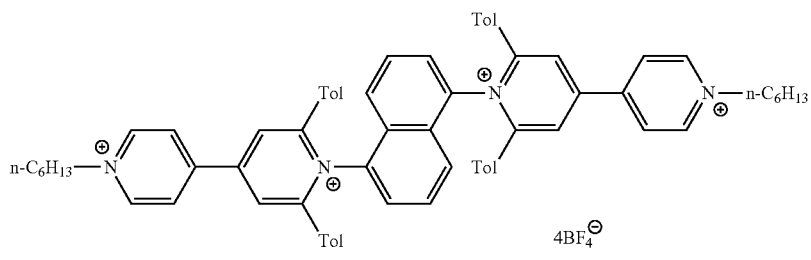 4BF$_4^\ominus$ |
| 1-11 | 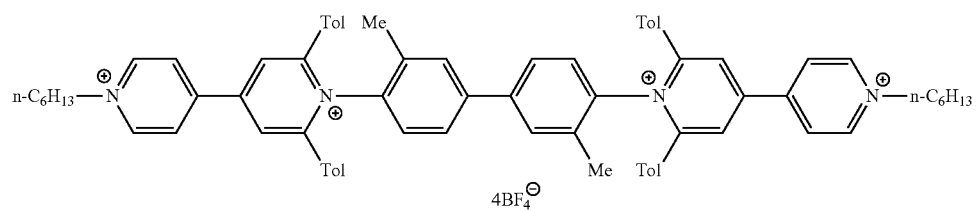 4BF$_4^\ominus$ |

-continued
| Compound | Formula |
|---|---|
| 1-12 | 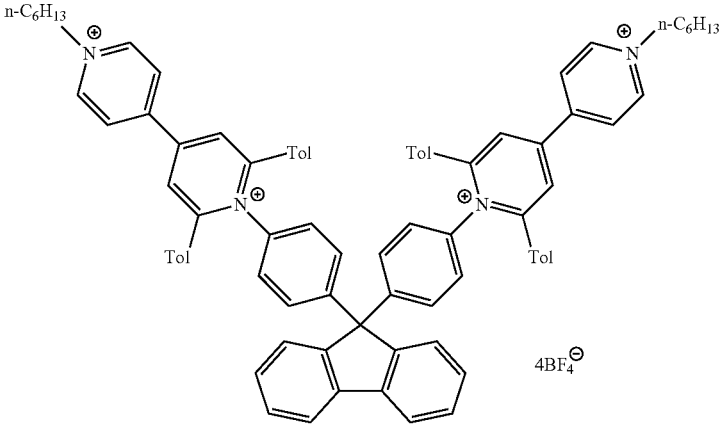 4BF$_4^\ominus$ |
| 1-13 | 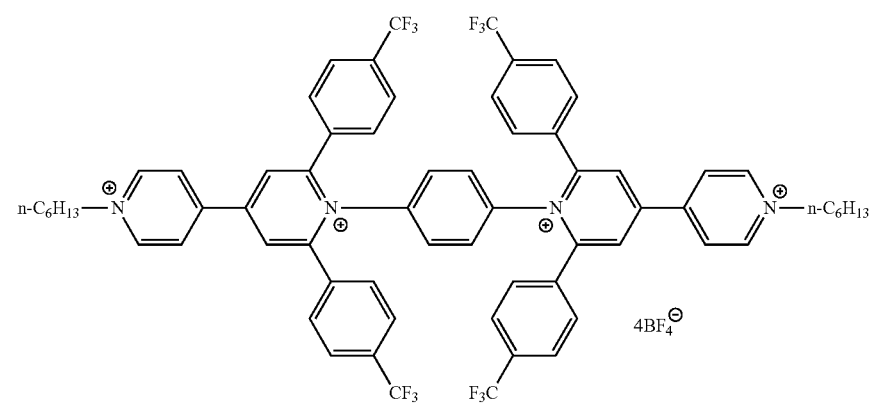 4BF$_4^\ominus$ |
| 1-14 | 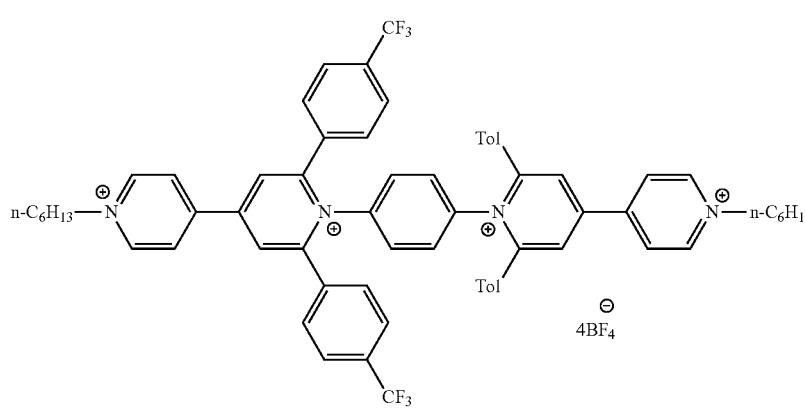 4BF$_4^\ominus$ |

-continued

| Compound | Formula |
|---|---|
| 2-1 |  |
| 2-2 | 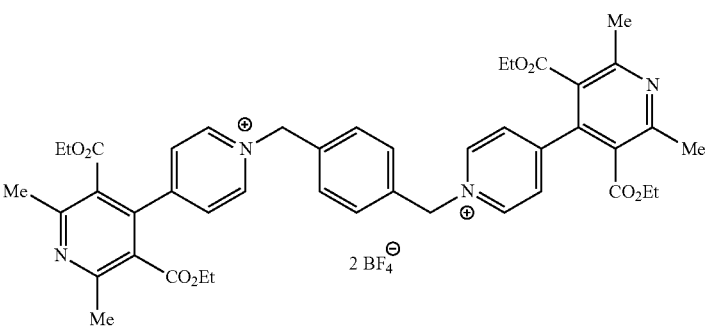 |

Me represents methyl;
Ph represents phenyl;
Tol represents 4-methylphenyl

Compounds represented by formula (I) may be prepared according to various methods well known in the art. However, the Applicant has found a particularly advantageous method for preparing compounds of formula (I-3). According to this new method, which is illustrated hereafter, a wide variety of useful alkyl, aryl and heteroaryl substituents can be readily introduced onto the C-atoms of the pyridine rings.

Such high flexibility is not possible according to the method disclosed in US 2009/0082570 A1. US 2009/0082570 A1 discloses a method of manufacturing a range of viologens which include a selection of arylene bridged violgens. Besides the series of bridged viologens is exemplified by symmetrically substituted arylene bridged viologens which are accessed from expensive commercially available 4,4'-bipyridine. Therefore, the present invention also relates to a method for preparing a compound of formula (I-3) in which A and B are nitrogen, $R^1$ and $R^2$ are identical and X is tetrafluoroborate comprising the step of reacting a 2,6-disubstituted-4-[(1H)-pyridinium-4-yl]pyrylium bis(tetrafluoroborate) (1) with a diamine (2):

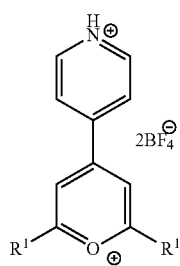

1

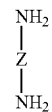

2 wherein Z, and $R^1$ are as defined above.

The use of a single 2,6-disubstituted-4-[(1H)-pyridinium-4-yl]pyrylium bis(tetrafluoroborate) (1) results in symmetrically substituted two-cores viologen derivatives (3) of formula (I-3) wherein A and B are nitrogen, and $R^1$ and $R^2$ are identical. Through a control the amount of the diamine (2) and a subsequent reaction with a second 2,6-disubstituted-4-[(1H)-pyridinium-4-yl]pyrylium bis(tetrafluoroborate) (1'), unsymmetrically substituted two-cores viologen derivatives (3') of formula (I-3) wherein A and B are nitrogen, and $R^1$ and $R^2$ are different can be obtained as shown on scheme A.

Scheme A

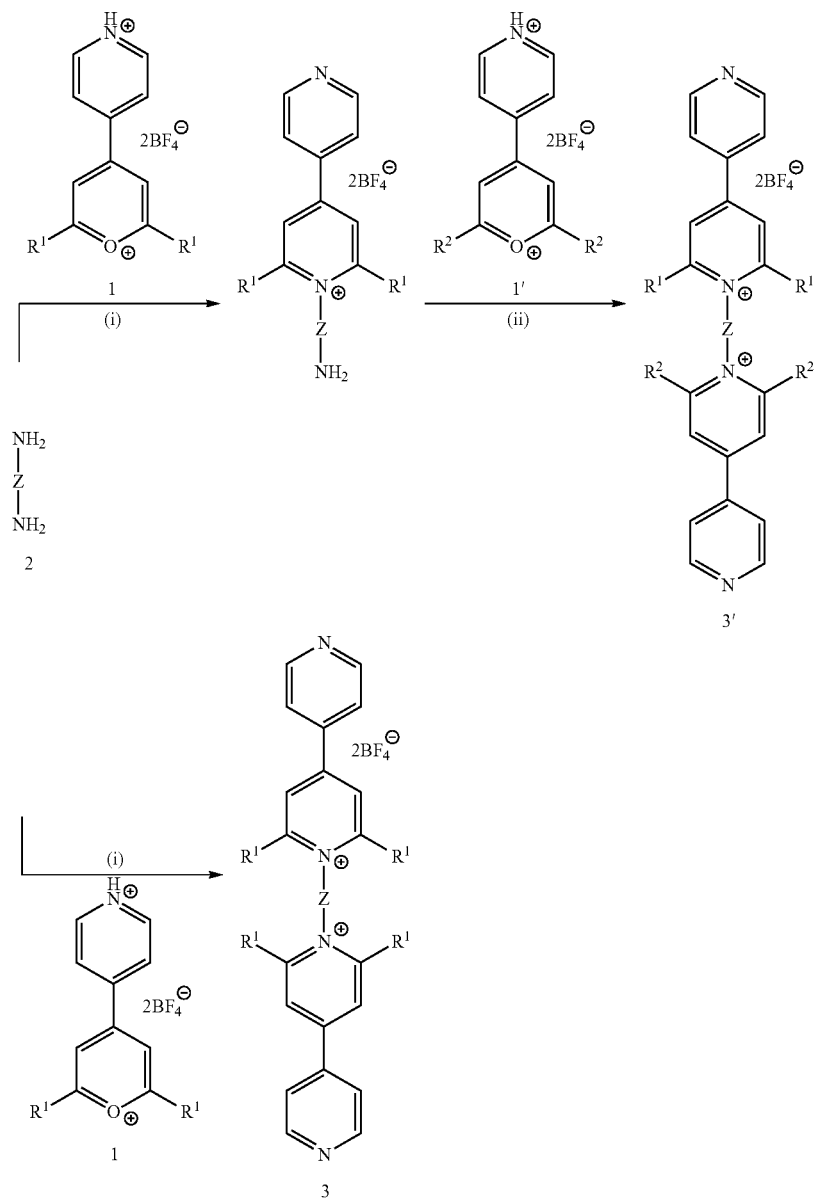

Steps (i) and (ii) disclosed in scheme A may be achieved under heat, for example from 70 to 90° C., in an alcohol and in the presence of a base.

Compounds of formula (I-3) wherein A and/or B are respectively —N$^+$(R$^{7a}$)— and —N$^+$(R$^{7b}$)— as defined above can be obtained from the corresponding compounds (3) or (3') using suitable reaction step well known in the art. For example, compounds of formula (I-3) wherein A and/or B are —N$^+$(alkyl)- can be obtained through an N-alkylation of the corresponding compound (3) or (3') with a suitable haloalkane.

The 2,6-disubstituted-4-[(1H)-pyridinium-4-yl]pyrylium bis(tetrafluoroborate) (1) may be prepared according to various methods well known in the art. For example, 4-(4-pyridyl)-1,5-disubstituted-1,5-diketones can be obtained by the condensation of pyridine-4-carboxaldehyde and substituted acetophenones (see for example Aryl-substituted Derivatives of 4,4'-Bipyridylium Salts: their Spectroscopic Properties and Stereochemistry, J. E. Downes, *J. Chem. Soc.* (C), 1967, 1491 and Pyrylogens: Synthesis, Structural, Electrochemical, and Photophysical Characterization of a New Class of Electron Transfer Sensitizers, E. L. Clennan, C. Liao, E. Ayokosok, *J. Am. Chem. Soc.*, 2008, 130, 7552). The cyclisation of the 4-(4-pyridyl)-1,5-disubstituted 1,5-diketones can be readily accomplished by, for example, heating in glacial acetic acid containing trans-chalcone and boron trifluoride etherate to give the 2,5-disubstituted 4-[(1H)-pyridinium-4-yl]pyrylium bis(tetrafluoroborates) (1).

Further specific examples of synthesis of compounds of the invention are illustrated below.

The present invention also relates to electrochromic compositions comprising at least one compound of formula (I) as defined above as an oxydizing electrochromic compound.

One or more additional oxidizing electrochromic compounds can be added to the composition of the invention so as to adapt the colour or the intensity of the coloured state of the composition. Said additional compound can be another compound of formula (I) or a different compound such as compatible dyes or pigments. For Example, the additional oxidizing electrochromic compound can be selected from alkylviologens, arylviologens, alkylarylviologens, anthraquinone and their derivatives. Preferably, the additional compound has a redox potential close to the compound of formula (I). The composition also comprises a reducing compound. The reducing compound can be also an electrochromic compound. Example of reducing compounds include 5,10-dihydrophenazine, phenazine, phenothiazine, N,N,N',N'-tetramethyl-p-phenylenediamine, thioanthrene, tetrathiafulvalene, ferrocene and their derivatives.

The composition of the invention may comprise a fluid, mesomorphous or gel host medium in which the electrochromic compounds are preferably dissolved. The fluid or mesomorphous host medium is preferably selected from the group consisting of organic solvents, liquid crystals, polymers or liquid crystal polymers and mixtures thereof.

Suitable solvents are redox-inert solvents which cannot react with the electrochromic compounds of the composition. Examples of suitable solvents are ethylene carbonate, propylene carbonate, γ-butyrolactone, γ-valerolactone, acetronitrile, propionitrile, benzonitrile, glutaronitrile, methylglutaronitrile, dimethylformamide, N-methylpyrrolidone, sulfolane, 3-methyl sulfolane, benzene, toluene, methyl ethyl ketone, acetone, ethanol, tetrahydrofurfuryl alcohol, 2-methoxyethyl ether, xylene, cyclohexane, 3-methylcyclohexanone, ethyl acetate, ethyl phenylacetate, tetrahydrofuran, methanol, methyl propionate, ethylene glycol ethylene carbonate, ionic liquids, and mixtures thereof. Preference is given to carbonate and particularly propylene carbonate.

The liquid crystal medium that may be used in the present invention includes, without being limited to, such materials as nematic or chiral nematic media.

The polymers that may be used in the present invention includes, without being limited to polymers which are soluble with the solvent, in particular PMMA or other acrylate polymers, polyurethane, polyethylene oxide, polypropylene oxide, polyvinyl acetate, poly(N-vinyl pyrrolidone), and polyvinylidene fluoride.

Alternatively a polymeric liquid crystal medium can be used as the host material. These liquid crystal, polymer polymeric liquid crystal media are generally used in combination with an organic solvent, for example one of the organic solvents mentioned above.

The present invention also relates to an electrochromic device comprising a compound of formula (I) or a composition according to the invention. Said device may be selected from an optical article, preferably an optical lens or an optical filter, a window, preferably an aircraft window, a visor, a mirror and a display, in particular a segmented or matrix display. Preferably, the electrochromic device of the invention is an optical article, more preferably an optical lens, and even more preferably an ophthalmic lens.

Non-limiting examples of ophthalmic lens include corrective and non-corrective lenses, including single vision or multi-vision lenses, which may be either segmented or non-segmented, as well as other elements used to correct, protect, or enhance vision, including without limitation contact lenses, intra-ocular lenses, magnifying lenses and protective lenses or visors. Non-limiting examples of display elements and devices include screens and monitors.

Non-limiting examples of windows include automotive, marine and aircraft windows, filters, shutters, and optical switches.

A preferred device for holding the composition of the invention in a mechanically stable can comprise a pair of opposed substrates having a gap there between for receiving the mixture of the host medium and said compound or said composition of the present invention, and a frame for holding said pair of substrates adjacent one another.

Another device of the present invention comprises an optical component provided with at least one transparent cell arrangement juxtaposed in a parallel direction to the surface thereof, as disclosed in WO 2006/013250, each cell being tightly closed and containing said fluid, mesomorphous or gel host medium and said at least one compound of the present invention. Other devices according to the invention can be a device as described in FR 2937154 or FR2950710 comprising at least one compound of the invention.

EXAMPLES

This invention will be further illustrated by the following non-limiting examples which are given for illustrative purposes only and should not restrict the scope of the appended claims.

Example 1

Synthesis of compound 1-1: 4,4'-(1,4-phenylene)-bis[(4-pyridyl)-2,6-diphenylpyridinium]bis(tetrafluoroborate)

Boron trifluoride diethyl etherate (9 equiv.) was added dropwise to a solution of the 1,5-bis(phenyl)-3-(4-pyridyl)pentan-1,5-dione (1 equiv.) and trans-chalcone (1.15 equiv.) in hot glacial acetic acid (9 mL). The solution was heated under reflux for 6 hours. After cooling to room temperature diethyl ether (50 mL) was added and the resulting red precipitate was collected by filtration under reduced pressure. The foregoing solid was crystallised from glacial acetic acid to afford 2,6-diphenyl-4-[(1H)-pyridinium-4-yl]pyrylium bis(tetrafluoroborates) as a bright orange powder (71%) after vacuum filtration and washing with anhydrous diethyl ether.

2,6-diphenyl-4-[(1H)-pyridinium-4-yl]pyrylium bis(tetrafluoroborate) (2.15 equiv.) and sodium acetate (8.5 equiv.) was added to a stirred solution of the 1,4-diaminobenzene (1.0 equiv.) in propan-2-ol (50 mL). The reaction mixture was then heated under reflux for 16 hours whereupon a pale cream/yellow precipitate had formed. Water (25 mL) was then added to the hot suspension and the reaction mixture was stirred at room temperature for 12 hours. The precipitate was collected by vacuum filtration and air dried and then dried at 20° C. under reduced pressure (1 mbar, Buchi Kugelrohr drying pistol) for 24 h to afford compound 1-1 as a yellow-beige powder (71%), mp=>360° C., $\nu_{max}$ 3057, 1629, 1594, 1572, 1547, 1496, 1406, 1231, 1049, 1028, 816, 757, 701, 614, 557, 508 cm$^-$, $\delta_H$ (300 MHz, d$_6$-DMSO) 7.25 (16H, m, Ar—H), 7.54 (8H, m, Ar—H), 8.23 (4H, d, J=6.3 Hz, N—CH=CH), 8.58 (4H, s, PhC=CH), 8.84 (4H, d, J=6.3 Hz, N—CH=CH).

Example 2

Synthesis of compound 1-4: 4,4'-(1,3-phenylene)-bis[(4-pyridyl)-2,6-diphenylpyridinium]bis(tetrafluoroborate)

Compound 1-2 was obtained through an equivalent synthesis to example 1 using 1,3-diaminobenzene instead of 1,4-diaminobenzene.

Example 3

Synthesis of compound 1-4: 4,4'-(1,3-phenylene)-bis[1'-n-hexyl-2,6-diphenylpyridinium]tetrakis(tetrafluoroborate)

A stirred solution of compound 1-2 (1 equiv.) and 1-iodohexane (4 equiv.) in acetonitrile (30 mL), protected from daylight, was heated under reflux for ca. 16 hours. The cooled solvent was evaporated to dryness and the residue dissolved in a minimum amount of methanol (ca. 15 mL) and added dropwise to a vigorously stirred solution of $NaBF_4$ (8-10 equiv.) in water (200 mL). The resulting yellow-orange precipitate was collected by vacuum filtration and washed thoroughly with cold water and dried at 20° C. under reduced pressure (1 mbar, Buchi Kugelrohr drying pistol) for 24 h. Compound 1-4 was obtained as a pale orange-fawn powder (77%), mp=212° C. softens, decomp. at 320° C., $v_{max}$ 3613, 3068, 2931, 2863, 1626, 1554, 1420, 1230, 1028, 849, 777, 764, 699, 519 $cm^{-1}$, $\delta_H$ (300 MHz, $d_4$-MeOH) 0.95 (6H, t, J=7.2 Hz, [$(CH_2)_5CH_3]_2$), 1.40 (12H, bs, [$(CH_2)_3]_2$), 2.09 (4H, bm, $(CH_2)_2$), 4.73 (4H, t, J=7.2 Hz, $(NCH_2)_2$), 7.05 (1H, app t, J=8.1 Hz, NC=CH—C$\underline{H}$), 7.15 (8H, m, Ar—H), 7.43 (8H, m, Ar—H), 7.57 (6H, m, Ar—H, NC=C$\underline{H}$—CH), 7.74 (1H, app t, J=1.8 Hz, NC—C$\underline{H}$=CN), 8.60 (4H, s, ArC=C$\underline{H}$), 8.69 (4H, d, J=6.6 Hz, NCH=C$\underline{H}$), 9.21 (4H, d, J=6.6 Hz, NC$\underline{H}$=CH), $\delta_C$ (75 MHz, $d_4$-MeOH) 14.27, 23.46, 26.88, 32.30, 32.51, 63.36, 128.76, 130.08, 130.29, 130.44, 130.55, 131.23, 132.18, 132.34, 133.75, 141.08, 146.87, 151.44, 152.43, 159.36. Found: $[M-3BF_4^-]^{3+}$ 316.1678; $C_{62}H_{62}B_4F_{16}N_4$ requires $[M-3BF_4^-]^{3+}$=316.1675.

Example 4

Synthesis of compound 1-3: 4,4'-(1,4-phenylene)-bis[1'-n-hexyl-2,6-diphenylpyridinium]tetrakis(tetrafluoroborate)

Compound 1-3 was obtained through an equivalent synthesis starting from compound 1-1 instead of compound 1-2.

Example 5

Synthesis of compound 1-5: 1,1''-(2-methylpentan-1,5-diyl)bis(2,6-di(p-tolyl)-[4,4'-bipyridin]-1-ium) bis(tetrafluoroborate)

2,6-di-p-tolyl-4-[(1H)-pyridinium-4-yl]pyrylium bis(tetrafluoroborate) was obtained from 1,5-di(p-tolyl)-3-(4-pyridyl)pentan-1,5-dione as a bright orange powder after crystallisation from glacial acetic acid (71%), through an equivalent synthesis to 2,6-diphenyl-4-[(1H)-pyridinium-4-yl]pyrylium bis(tetrafluoroborates) of example 1.

A mixture of 2,6-di-p-tolyl-4-[(1H)-pyridinium-4-yl] pyrylium bis(tetrafluoroborate) (2.10 g, 4.1 mmol), 2-methylpentan-1,5-diamine (0.21 g, 1.8 mmol) and NaOAc (1.34 g, 16.3 mmol) in isopropanol (30 mL) was heated at reflux for 16 h. After cooling, water (40 mL) was added and the resulting precipitate filtered, washed with water (2×20 mL) and air dried to give the compound 1-5 (1.10 g, 65%) as a grey powder.

Example 6

Synthesis of compound 1-6: 4,4'-(1,5-naphthylene)-bis[2,6-di(p-tolyl)pyridinium]tetrakis(tetrafluoroborate)

2,6-di-p-tolyl-4-[(1H)-pyridinium-4-yl]pyrylium bis(tetrafluoroborate) (2.15 equiv.) and sodium acetate (8.5 equiv.), obtained from 1,5-di-p-tolyl-3-(4-pyridyl)pentan-1,5-dione, was added to a stirred solution of the 1,5-diaminonaphtalene (1.0 equiv.) in propan-2-ol (50 mL). The reaction mixture was then heated under reflux for ca. 16 hours whereupon a pale cream/yellow precipitate had formed. Water (25 mL) was then added to the hot suspension and the reaction mixture was stirred at room temperature for ca. 12 hours. The precipitate was collected by vacuum filtration, washed with aqueous ethanol and air dried to give compound 1-6.

Example 7

Synthesis of compound 1-7: 1,1''-(2-methylpentan-1,5-diyl)bis(2,6-di(p-tolyl)-[4,4'-bipyridin]-1-ium) tetrakis(tetrafluoroborate)

A solution of compound 1-5 obtained in example 5 (1.10 g, 1.2 mmol) and 1-iodohexane (1 g, 4.7 mmol) in MeCN (20 mL) was heated at reflux for 16 h, cooled and the volume reduced (to ~10 mL) and $Et_2O$ (60 mL) added. The mixture was stirred for 1 h and decanted. Fresh $Et_2O$ was added and decanted and the residue was air dried, dissolved in MeOH (5 mL) and added dropwise to a solution of $NaBF_4$ (6.6 g, 60 mml) in water (200 mL) with rapid stirring. The product was filtered, washed with water (3×20 mL) and air dried to give compound 1-7 (0.89 g, 56%) as an orange powder, $\delta_H$ (400 MHz, $CD_3OD$) 9.07-9.13 (4H, m, NC$\underline{H}$=CH), 8.58 (2H, d, J=6.8 Hz, NCH=C$\underline{H}$), 8.582 (2H, d, J=6.8 Hz, NCH=C$\underline{H}$), 8.37 (2H, s, NC(Tol)=CH), 8.34 (2H, s, NC(Tol)=CH), 7.60-7.50 (8H, m, Ar—H), 7.45-7.35 (8H, m, Ar—H), 4.70-4.10 (8H, m, $NCH_2$), 2.42 (6H, s, Ar-Me), 2.40 (6H, s, Ar-Me), 2.10-1.90 (7H, m, aliphatic-H), 1.40-0.70 (23H, m, aliphatic-H).

Example 8

Synthesis of compound 1-8: 4,4'-(1,4-phenylene)-bis[1'-n-hexyl-2,6-di(p-tolyl)pyridinium]tetrakis(tetrafluoroborate)

4,4'-(1,4-phenylene)-bis[(4-pyridyl)-2,6-di(p-tolyl)-pyridinium]bis(tetrafluoroborate) was obtained through an equivalent synthesis to example 1 starting from 2,6-di(p-tolyl)-4-[(1H)-pyridinium-4-yl]pyrylium bis(tetrafluoroborate), obtained from 1,5-di(p-tolyl)-3-(4-pyridyl)pentan-1,5-dione.

Compound 1-8 was obtained, through an equivalent synthesis to example 3 starting from 4,4'-(1,4-phenylene)-bis[(4-pyridyl)-2,6-di(p-tolyl)-pyridinium]bis(tetrafluoroborate) instead of compound 1-2, as a pale orange powder (63%), mp=223° C. softens, decomp. at 293° C., $v_{max}$ 3617, 3066, 2929, 2863, 1626, 1552, 1514, 1229, 1027, 858, 814, 520 $cm^-$, $\delta_H$ (300 MHz, $d_4$-MeOH) 0.94 (6H, t, J=7.2 Hz,

[(CH$_2$)$_5$C$\underline{H}_3$]$_2$), 1.40 (12H, bs, [(CH$_2$)$_3$]$_2$), 2.09 (4H, bs, (CH$_2$)$_2$), 2.51 (12H, s, 4-C$\underline{H}_3$C$_6$H$_4$), 4.73 (4H, t, J=7.2 Hz, (NCH$_2$)$_2$), 7.24 (16H, m, 4-CH$_3$C$_6$$\underline{H}_4$), 7.48 (4H, s, N—C$_6$H$_4$—N), 8.54 (4H, s, ArC=CH), 8.68 (4H, d, J=6.6 Hz, NCH=C$\underline{H}$), 9.20 (4H, d, J=6.6 Hz, NC$\underline{H}$=CH), δ$_C$ (75 MHz, d$_4$-MeOH) 14.25, 21.69, 23.46, 26.88, 32.29, 32.50, 63.33, 128.66, 129.97, 130.68, 130.98, 131.07, 131.13, 141.74, 142.45, 146.87, 151.44, 151.79, 159.53. Found: [M-3BF$_4$]$^{3+}$=334.8549; C$_{66}$H$_{70}$B$_4$F$_{16}$N$_4$ requires [M-3BF$_4^-$]$^{3+}$=334.8550.

Example 9

Synthesis of compound 1-9: 4,4'-(1,3-phenylene)-bis[1'-n-hexyl-2,6-di(p-tolyl)pyridinium]tetrakis(tetrafluoroborate)

Compound 1-9 was obtained through an equivalent synthesis to example 8 using 1,3-diaminobenzene instead of 1,4-diaminobenzene.

Example 10

Synthesis of compound 1-10: 4,4'-(1,5-naphthylene)-bis[1'-n-hexyl-2,6-di(p-tolyl)pyridinium]tetrakis(tetrafluoroborate)

A stirred solution of compound 1-6 (1 equiv.), obtained in example 6, and 1-iodohexane (4 equiv.) in acetonitrile (30 mL), protected from daylight, was heated under reflux for ca. 16 hours. The cooled solvent was diluted with diethyl ether and the resulting precipitate was collected by vacuum filtration, washed with a minimum amount of diethyl ether and air dried. The foregoing precipitate was dissolved in a minimum amount of methanol (ca. 15 mL) and added dropwise to a vigorously stirred solution of NaBF$_4$ (8-10 equiv.) in water (200 mL). The resulting precipitate was collected by vacuum filtration and washed thoroughly with cold water and dried at 20° C. Compound 1-10 was obtained as a pale orange powder (41%), ν$_{max}$ 3069, 2930, 2867, 1627, 1553, 1511, 1021, 822, 797, 520 cm$^{-1}$, δ$_H$ (300 MHz, d$_6$-DMSO) 0.88 (6H, t, J=7.6 Hz, [(CH$_2$)$_5$C$\underline{H}_3$]$_2$), 1.33 (12H, bs, [(CH$_2$)$_3$]$_2$), 2.06 (4H, bs, (CH$_2$)$_2$), 2.33 (12H, s, 4-C$\underline{H}_3$—C$_6$H$_4$), 4.71 (4H, t, J=7.2 Hz, (NCH$_2$)$_2$), 7.01 (16H, m, Ar—H), 7.58 (4H, m, Ar—H), 8.05 (2H, d, J=7.2 Hz, Ar—H), 8.91 (4H, s, Ar—C=CH), 9.02 (4H, d, J=6.6 Hz, NCH=C$\underline{H}$), 9.42 (4H, d, J=6.6 Hz, NC$\underline{H}$=CH), δ$_C$ (75 MHz, d$_6$-DMSO) 13.8, 21.0, 21.8, 25.1, 30.5, 30.7, 61.0, 124.8, 127.0, 127.4, 128.0, 128.3, 128.5, 129.1, 129.2, 130.1, 134.9, 140.5, 145.8, 148.1, 149.8, 157.6. Found: [M-3BF$_4^-$]$^{3+}$=351.5269; C$_{70}$H$_{72}$BF$_4$N$_4$ requires [M-3BF$_4^-$]$^{3+}$=351.5279.

Example 11

Synthesis of compound 1-11: 4,4'-(2,2'-dimethyl-4,4'-biphenylene)-bis[1'-n-hexyl-2,6-di(4-methylphenyl)pyridinium]tetrakis(tetrafluoroborate)

4,4'-(2,2'-dimethyl-4,4'-biphenylene)-bis[2,6-di(4-methylphenyl)pyridinium]tetrakis(tetrafluoroborate) was obtained, through an equivalent synthesis to examples 6 using 3,3'-dimethyl-biphenyl-4,4'-diamine instead of 1,5-diaminonaphtalene.

Compound 1-11 was obtained from 4,4'-(2,2'-dimethyl-4,4'-biphenylene)-bis[2,6-di(4-methylphenyl)pyridinium]tetrakis(tetrafluoroborate), through an equivalent synthesis to example 10, as a tan powder (85%), ν$_{max}$ 3073, 2928, 2862, 1625, 1551, 1423, 1021, 853, 822, 519 cm$^-$, δ$_H$ (300 MHz, d$_6$-DMSO) 0.87 (6H, t, J=7.6 Hz, [(CH$_2$)$_5$C$\underline{H}_3$]$_2$), 1.32 (12H, bs, [(CH$_2$)$_3$]$_2$), 1.91 (6H, s, (biphenyl-CH$_3$)$_2$), 2.01 (4H, bs, (CH$_2$)$_2$), 2.29 (12H, s, 4-C$\underline{H}_3$—C$_6$H$_4$), 4.71 (4H, t, J=7.2 Hz, (NCH$_2$)$_2$), 7.22 (8H, m, Ar—H), 7.38 (8H, m, Ar—H), 7.51 (4H, m, Ar—H), 7.80 (2H, d, J=8.4 Hz, Ar—H), 8.92 (4H, s, Ar—C=CH), 9.02 (4H, d, J=6.9 Hz, NCH=C$\underline{H}$), 9.43 (4H, d, J=6.9 Hz, NC$\underline{H}$=CH), δ$_C$ (75 MHz, d$_6$-DMSO) 13.8, 17.2, 20.8, 21.0, 25.1, 30.5, 30.7, 61.0, 124.0, 127.0, 128.1, 128.7, 128.9, 129.2, 129.6, 130.4, 133.8, 137.9, 138.8, 140.9, 145.7, 148.3, 149.4, 157.1. Found: [M-3BF$_4^-$]$^{3+}$=369.5432; C$_{74}$H$_{78}$BF$_4$N$_4$ requires [M-3BF$_4^-$]$^{3+}$=369.5425.

Example 12

Synthesis of compound 1-12: 4,4'-(9H-fluorene-9,9-diyl)-bis(1,4-phenylene)-bis[1'-n-hexyl-2,6-di(4-methylphenyl)pyridinium]tetrakis(tetrafluoroborate)

4,4'-(9H-fluorene-9,9-diyl)-bis(1,4-phenylene)-bis[2,6-di(4-methylphenyl)pyridinium]tetrakis(tetrafluoroborate) was obtained, through an equivalent synthesis to examples 6 using 9H-fluorene-9,9-diamine instead of 1,5-diaminonaphtalene.

Compound 1-12 was obtained from 4,4'-(9H-fluorene-9,9-diyl)-bis(1,4-phenylene)-bis[2,6-di(4-methylphenyl)pyridinium]tetrakis(tetrafluoroborate), through an equivalent synthesis to example 10, as a pale yellow powder (96%), δ$_H$ (300 MHz, d$_6$-DMSO) 0.88 (6H, t, J=7.2 Hz, [(CH$_2$)$_5$C$\underline{H}_3$]$_2$), 1.31 (12H, bs, [(CH$_2$)$_3$]$_2$), 1.99 (4H, bm, (CH$_2$)$_2$), 2.28 (12H, s, 4-C$\underline{H}_3$—C$_6$H$_4$), 4.70 (4H, t, J=7.5 Hz, (NCH$_2$)$_2$), 6.62 (4H, d, J=8.7 Hz, Ar—H), 7.08 (2H, d, J=7.5 Hz, Ar—H), 7.16 (8H, m, Ar—H) 7.24 (12H, m, Ar—H), 7.33 (2H, app. t, Ar—H), 7.44 (2H, app. t, Ar—H), 7.89 (2H, d, J=7.2 Hz, Ar—H), 8.88 (4H, s, Ar—C=CH), 9.02 (4H, d, J=6.9 Hz, NCH=C$\underline{H}$), 9.42 (4H, d, J=6.9 Hz, NC$\underline{H}$=CH).

Example 13

Synthesis of compound 1-13: 4,4'-(1,4-phenylene)-bis[1'-n-hexyl-2,6-di(4-trifluoromethylphenyl)pyridinium]tetrakis(tetrafluoroborate)

4,4'-(1,4-phenylene)-bis[(4-pyridyl)-2,6-di(4-trifluoromethylphenyl)pyridinium]bis(tetrafluoroborate) was obtained through an equivalent synthesis to example 1 starting from 2,6-di(4-trifluoromethylphenyl)-4-[(1H)-pyridinium-4-yl]pyrylium bis(tetrafluoroborate), obtained from 1,5-di(4-trifluoromethylphenyl)-3-(4-pyridyl)pentan-1,5-dione.

Compound 1-13 was obtained, through an equivalent synthesis to example 3 starting from 4,4'-(1,4-phenylene)-bis[(4-pyridyl)-2,6-di(4-trifluoromethylphenyl)pyridinium]bis(tetrafluoroborate) instead of compound 1-2, as a pale pink powder (50%), mp=275.7° C. decomp., ν$_{max}$ 3072, 2935, 2867, 1632, 1619, 1558, 1322, 1111, 1031, 833, 666, 520 cm$^{-1}$, δ$_H$ (300 MHz, d$_4$-MeOH) 0.91 (6H, bs, [(CH$_2$)$_5$CH$_3$]$_2$), 1.38 (12H, bs, [(CH$_2$)$_3$]$_2$), 2.06 (4H, bs, (CH$_2$)$_2$), 4.70 (4H, bs, (NCH$_2$)$_2$), 7.61 (20H, m, 4-CF$_3$C$_6$$\underline{H}_4$, N—C$_6$$\underline{H}_4$—N), 8.66 (4H, bs, NCH=C$\underline{H}$), 8.70 (4H, s, ArC=CH), 9.19 (4H, d, J=4.5 Hz, NC$\underline{H}$=CH), δ$_C$ (75 MHz, d$_6$-DMSO) 11.50, 20.71, 24.14, 29.54, 29.76, 60.69, 120.48, 124.08, 124.22, 126.02, 128.25, 128.65, 129.17, 130.56, 131.00, 134.74, 138.66, 144.25, 148.21, 150.24,

Example 14

Synthesis of compound 1-14: 1-{4-[1'-n-hexyl-2,6-di(4-methylphenyl)pyridinium]}-4-{4'-[1'-n-hexyl-2,6-di(4-trifluoromethylphenyl)pyridinium]}phenylene tetrakis(tetrafluoroborate)

2,6-Di(4-methylphenyl)-4-[(1H)-pyridinium-4-yl]pyrylium bis(tetrafluoroborate), prepared as outlined in Example 5, (3.00 g, 5.8 mmol) was added portionwise to a warm (80° C.) stirred solution of 1,4-diaminobenzene (3.79 g, 35.0 mmol) and sodium acetate (0.96 g, 11.7 mmol) in propan-2-ol (30 mL). Upon completion of the addition of the 2,6-di(4-methylphenyl)-4-[(1H)-pyridinium-4-yl]pyrylium bis(tetrafluoroborate) the reaction mixture was stirred at 80° C. for 3 hours. After cooling the precipitated solid was collected by vacuum filtration. The precipitate was then washed with propan-2-ol/water to give the 1-(4-aminophenyl)-2,6-di(4-methylphenyl)-4-(4-pyridyl)pyridinium tetrafluoroborate after drying as a pale brown powder (89%), mp=172-176° C., $v_{max}$ 3488, 3392, 3034, 1621, 1597, 1513, 1402, 1312, 1235, 1094, 1050, 988, 893, 814, 539, 517 cm$^-$, $\delta_H$ (300 MHz, d$_4$-MeOH) 2.35 (6H, s, CH$_3$C$_6$H$_4$), 6.40 (2H, m, H$_2$NC—C$\underline{H}$), 6.89 (2H, m, H$_2$NC—C=C$\underline{H}$), 7.10 (4H, m, CH$_3$C—C$\underline{H}$=CH), 7.32 (4H, m, CH$_3$C—CH=C$\underline{H}$), 8.09 (2H, dd, J=4.5, 1.8 Hz, N—CH=C$\underline{H}$), 8.49 (2H, s, ArC=C$\underline{H}$), 8.83 (2H, dd, J=4.5, 1.8 Hz, N—C$\underline{H}$=CH), NH$_2$ signal absent in d$_4$-MeOH due to exchange but resonates as a broadened singlet at δ 3.87 in CDCl$_3$, $\delta_C$ (75 MHz, d$_4$-MeOH) 21.34, 114.63, 118.49, 123.89, 127.68, 129.74, 130.11, 130.34, 130.92, 131.96, 141.94, 144.16, 151.15, 151.68, 154.69, 159.73. Found: [M−BF$_4^-$]$^+$=428.2115; C$_{30}$H$_{26}$BF$_4$N$_3$ requires [M−BF$_4^-$]$^+$=428.2121.

2,6-Di(4-trifluoromethylphenyl)-4-[(1H)-pyridinium-4-yl]pyrylium bis(tetrafluoroborate) (1.1 equiv.) and sodium acetate (5 equiv.) was added to a stirred solution of the foregoing 1-(4-aminophenyl)-2,6-di(4-methylphenyl)-4-(4-pyridyl)pyridinium tetrafluoroborate (1.0 equiv.) in propan-2-ol (50 mL). The reaction mixture was then heated under reflux for 15 hours whereupon a pale cream coloured precipitate had formed. Water (30 mL) was then added to the hot suspension and the reaction mixture was stirred at room temperature for 12 hours. The precipitate, 1-{4-[(4-pyridyl)-2,6-di(4-methylphenyl)pyridinium]}-4-{4'-[(4-pyridyl)-2,6-di(4-trifluoro-methylphenyl)pyridinium]}phenylene bis(tetrafluoroborate), was collected by vacuum filtration and air dried and then dried at 20° C. under reduced pressure (1 mbar, Buchi Kugelrohr drying pistol) for 24 h. A stirred solution of the foregoing dried 1-{4-[(4-pyridyl)-2,6-di(4-methylphenyl)pyridinium]}-4-{4'-[(4-pyridyl)-2,6-di(4-trifluoromethylphenyl)pyridinium]}phenylene bis(tetrafluoroborate) (1 equiv.) and 1-iodohexane (4 equiv.) in acetonitrile (35 mL), protected from daylight, was heated under reflux for 20 hours. The cooled solvent was evaporated to dryness and the residue dissolved in a minimum amount of methanol (10 mL) and added dropwise to a vigorously stirred solution of NaBF$_4$ (8 equiv.) in water (200 mL). The resulting yellow-orange precipitate was collected by vacuum filtration and washed thoroughly with cold water and dried at 20° C. under reduced pressure (1 mbar, Buchi Kugelrohr drying pistol) for 24 h to afford compound 1-14 as a pale brown powder 91%, mp=295-297° C., $\delta_H$ (300 MHz, d$_4$-MeOH) 0.94 (6H, t, J=7.2 Hz, [(CH$_2$)$_5$C$\underline{H}_3$]$_2$), 1.42 (12H, bm, [(CH$_2$)$_3$]$_2$), 2.09 (4H, bm, (CH$_2$)$_2$), 2.49 (6H, s, 4-C$\underline{H}_3$C$_6$H$_4$), 4.73 (4H, t, J=7.2 Hz, (NCH$_2$)$_2$), 7.25 (8H, m, 4-CH$_3$C$_6$H$_4$), 7.53 (4H, s, N—C$_6$H$_4$—N), 7.60 (4H, m, F$_3$C—C—C$\underline{H}$=CH), 7.69 (4H, m, F$_3$C—C—CH=C$\underline{H}$), 8.64 (2H, s, Tol-C=C$\underline{H}$), 8.69 (4H, m, NCH=C$\underline{H}$), 8.75 (2H, s, 4-CF$_3$C$_6$H$_4$—C=C$\underline{H}$), 9.21 (4H, m, NC$\underline{H}$=CH), $\delta_C$ (75 MHz, d$_6$-DMSO) 13.77, 20.68, 21.82, 25.08, 30.51, 30.68, 61.06, 121.89, 125.51, 126.93, 128.10, 128.85, 128.95, 129.22, 129.60, 129.70, 129.81, 130.24, 130.69, 136.21, 139.06, 140.18, 140.49, 145.75, 145.91, 147.37, 147.88, 148.90, 149.38, 155.60, 157.08. Found: [M−2BF$_4^-$]$^{2+}$=599.2575; C$_{66}$H$_{64}$B$_4$F$_{22}$N$_4$ requires [M−2BF$_4^-$]$^{2+}$=599.2578.

Example 15

Synthesis of compound 2-1: 1,1"-(1,3-phenylenebis(methylene))bis(3',5'-bis(ethoxycarbonyl)-2',6'-dimethyl-[4,4'-bipyridin]-1-ium) bis-tetrafluoroborate)

m-Xylene dibromide (0.66 g, 2.5 mmol) and diethyl 2,6-dimethyl-4,4'-bipyridine-3,5-dicarboxylate (3.28 g, 10 mmol) were refluxed in MeCN (50 mL). After 2 days the solvent was removed under reduced pressure and residue was crystallised from DCM-hexane by slow evaporation to give the dibromide salt (2.17 g, 94%) as a cream powder. The foregoing dibromide salt (1 g, 1.1 mmol) was dissolved in water (10 mL) and added dropwise to a solution of sodium tetrafluoroborate (1.43 g, 13 mmol) in water (10 mL) with stirring. After 0.5 h the precipitate was filtered off and dried to give compound 2-1 (0.82 g, 81%) as tan needles, $\delta_H$ (400 MHz, d$_6$-DMSO) 9.32 (4H, d, J=6.8 Hz, NC$\underline{H}$=CH), 8.22 (4H, d, J=6.8 Hz, NCH=C$\underline{H}$), 7.91 (1H, s, Ar—H), 7.70-7.50 (3H, m, Ar—H), 5.94 (4H, s, NCH$_2$), 3.98 (8H, q, J=7.2 Hz, OC$\underline{H}_2$CH$_3$), 2.62 (12H, s, CH$_3$), 0.768 (12H, t, J=7.2 Hz, OCH$_2$C$\underline{H}_3$).

Example 16

Synthesis of compound 2-2: 1,1"-(1,4-phenylenebis(methylene))bis(3',5'-bis(ethoxycarbonyl)-2',6'-dimethyl-[4,4'-bipyridin]-1-ium) bis-tetrafluoroborate)

p-Xylene dibromide (0.5 g, 1.9 mmol) and diethyl 2,6-dimethyl-4,4'-bipyridine-3,5-dicarboxylate (1.86 g, 5.7 mmol) was refluxed in MeCN (50 mL). After 16 h, the mixture was cooled, filtered and washed with acetone (30 mL) and Et$_2$O (30 mL) and air dried to give the dibromide salt (1.6 g, 92%) as a colourless powder. The foregoing dibromide salt (1 g, 1.1 mmol) was dissolved in MeOH-water (100 mL, 1:4) and added dropwise to sodium tetrafluoroborate (7.2 g, 65 mmol) in water (350 mL) to give, in the same manner as described for example 15, compound 2-2 (0.87 g, 96%) as tan needles, $\delta_H$ (400 MHz, d$_6$-DMSO) 9.32 (4H, d, J=6.8 Hz, NC$\underline{H}$=CH), 8.20 (4H, d, J=6.8 Hz, NCH=C$\underline{H}$), 7.69 (4H, s, Ar—H), 5.92 (4H, s, NCH$_2$), 3.97 (8H, q, J=7.2 Hz, OC$\underline{H}_2$CH$_3$), 2.61 (12H, s, CH$_3$), 0.76 (12H, t, J=7.2 Hz, OCH$_2$C$\underline{H}_3$).

Example 17

Evaluation of Oxydo-Reduction Potential and of the Absorption Spectrum of the Compounds of the Invention The oxydo-reduction potentials of the compounds are measured by a method of cyclic voltammetry with 3 electrodes.

The 3 electrodes used are:
1 Platinum working electrode
1 Platinum auxiliary or counter electrode
1 Platinum reference electrode which is immersed into a solution consisting of 0.01M AgNO$_3$+0.1M TBAP (tetrabutylammonium perchlorate) in acetonitrile.

The potential values indicated are the first oxidative potential for the compounds, with regards to the standard hydrogen reference electrode (SHE).

The analyzed solution comprises 0.01M of the compound to be analyzed and 1M of TBAP salt.

The scan rate of the potential is fixed to 100 mV/s.

The absorption spectra of the compounds are measured with a solution comprising 0.01M of the compound to be analyzed, 0.02M Phenothiazine (Phtz) or 10-Methylphenothiazine (Mephtz) and 1M of TBAP salt in propylene carbonate as solvent.

This solution is introduced into a quartz tank where at least one glass electrode coated with Indium Tin Oxide (ITO) is placed in order to colour the analyzed compound on this electrode. The absorption spectrum of the compound in the time domain is measured by a spectrophotometer.

The reductive agent (phenothiazine for all compounds except compounds 1-6 and 1-7 using 10-methylphenothiazine) is colouring on another glass electrode coated with Indium Tin Oxide (ITO).

The potential applied between both electrodes, for activating the compounds, is equal to the addition, in absolute value, of $E^1_{red}$ of the compound+$E^1_{ox}$ of phenothiazine (which is $E^1_{ox}$=0.36V) or methylphenothiazine (which is $E^1_{ox}$=0.45V).

The absorption spectrum is read after 3 min of activation, in particular the $\lambda_{max}$ value, which corresponds to the maximum absorption peak within the visible spectrum (between 400 and 800 nm).

The results for each of the synthesized compounds are indicated in Table 1 below. $E^1_{red}$ corresponds to the first oxidative potential. The colour indicated in Table 1 is the visual colour perceived by emmetropic eyes under the day light. It should be noted that the $\lambda_{max}$ value is just orienting the colour of the molecule, but the whole absorption spectrum has to be taken into account in order to understand the final perceived colour of one compound.

TABLE 1

| Compound | Formula | $E^1_{red}$ (V) | $\lambda_{max}$ (nm) | Colour |
|---|---|---|---|---|
| 1-1 | Bis-(2,6-diphenyl-4-(pyridin-4-yl)pyridinium) linked by 1,4-phenylene, 2BF$_4^-$ | −0.73 | 544 | red |
| 1-2 | Bis-(2,6-diphenyl-4-(pyridin-4-yl)pyridinium) linked by 1,3-phenylene, 2BF$_4^-$ | −0.70 | 420 | Yellow |
| 1-3 | N,N'-di-n-C$_6$H$_{13}$ bis-(2,6-diphenyl-4-(pyridin-4-yl)pyridinium) linked by 1,4-phenylene, 4BF$_4^-$ | −0.76 | 629 | green |
| 1-4 | N,N'-di-n-C$_6$H$_{13}$ bis-(2,6-diphenyl-4-(pyridin-4-yl)pyridinium) linked by 1,3-phenylene, 4BF$_4^-$ | −0.76 | 630 | green |

TABLE 1-continued

| Compound | Formula | $E^1_{red}$ (V) | $\lambda_{max}$ (nm) | Colour |
|---|---|---|---|---|
| 1-5 | [structure with two pyridinium centers bridged by methyl-substituted alkyl chain, Tol substituents, 2 BF$_4^{\ominus}$] | −0.79 | 721 | green |
| 1-6 | [structure with naphthalene bridge between two pyridinium units, Tol substituents, 2BF$_4^{\ominus}$] | −0.75 | 547 | red |
| 1-7 | [structure with n-C$_6$H$_{13}$ terminal groups, methyl-substituted alkyl bridge, Tol substituents, 2 BF$_4^{\ominus}$] | −0.8 | 741 | green |
| 1-8 | [structure with n-C$_6$H$_{13}$ terminal groups, phenylene bridge, Tol substituents, 4BF$_4^{\ominus}$] | −0.78 | 643 | green |
| 1-9 | [structure with n-C$_6$H$_{13}$ terminal groups, meta-phenylene bridge, Tol substituents, 4BF$_4^{\ominus}$] | −0.78 | 628 | green |
| 1-10 | [structure with n-C$_6$H$_{13}$ terminal groups, naphthalene bridge, Tol substituents, 4BF$_4^{\ominus}$] | −0.77 | 628 | green |
| 1-11 | [structure with n-C$_6$H$_{13}$ terminal groups, Me-substituted biphenyl bridge, Tol substituents, 4BF$_4^{\ominus}$] | −0.79 | 643 | green |

TABLE 1-continued
| Compound | Formula | $E^1_{red}$ (V) | $\lambda_{max}$ (nm) | Colour |
|---|---|---|---|---|
| 1-12 | 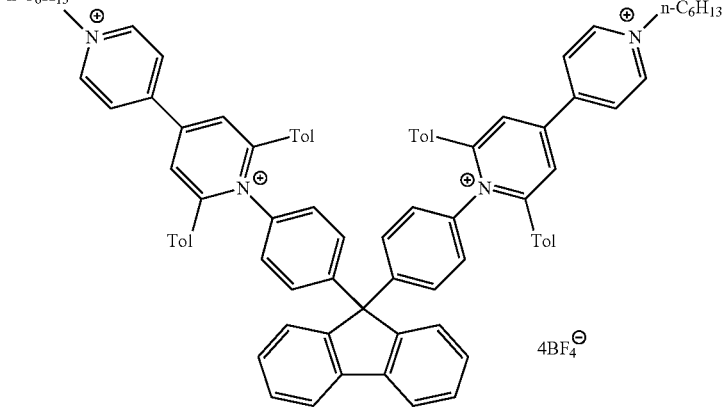 | −0.81 | 632 | green |
| 1-13 | 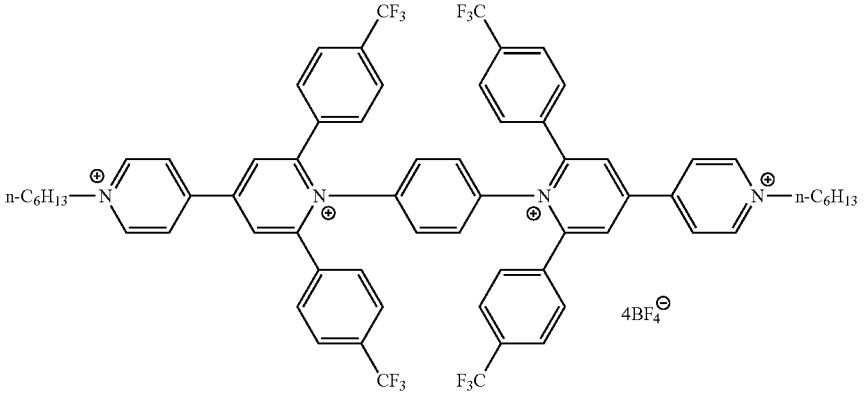 | −0.65 | 642 | green |
| 1-14 | 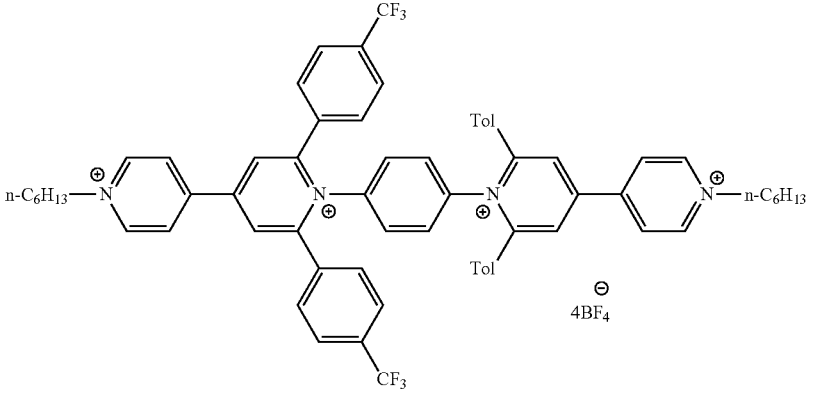 | / | / | / |
| 2-1 | 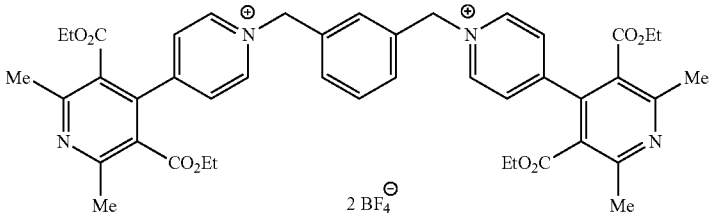 [SMILES: CCOC(=O)c1c(C)nc(C)c(C(=O)OCC)c1-c1cc[n+](Cc2cccc(C[n+]3ccc(-c4c(C(=O)OCC)c(C)nc(C)c4C(=O)OCC)cc3)c2)cc1] | −1.35 | / | / |

TABLE 1-continued

| Compound | Formula | $E^1_{red}$ (V) | $\lambda_{max}$ (nm) | Colour |
|---|---|---|---|---|
| 2-2 | 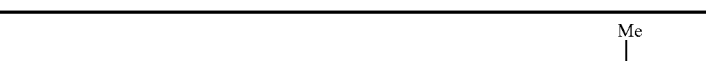 | −1.34 | / | / |

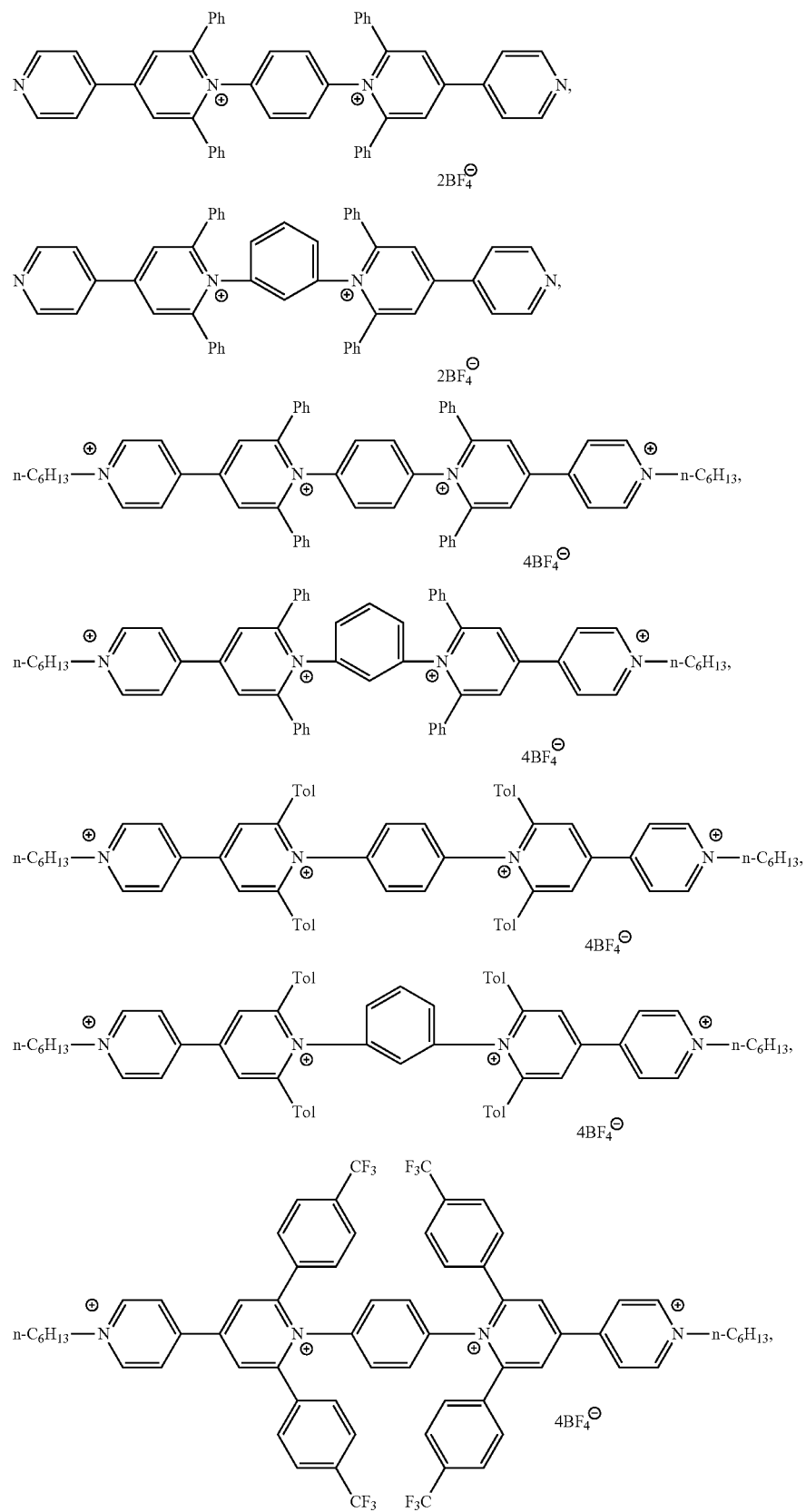

-continued
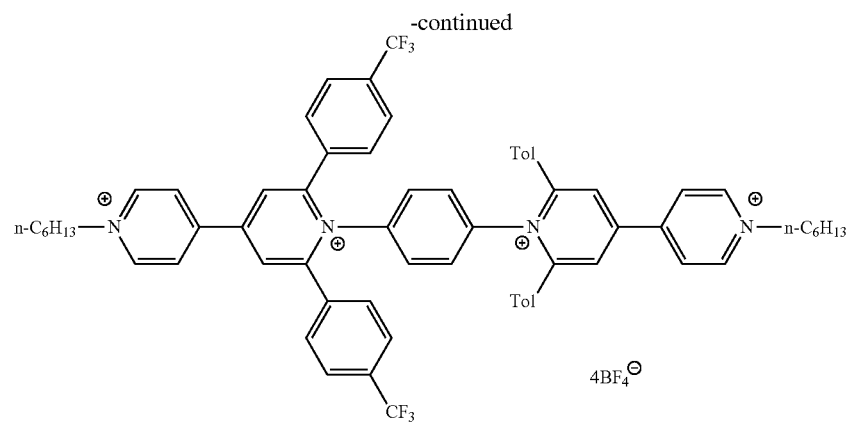

The invention claimed is:

1. A compound of formula (I-1):

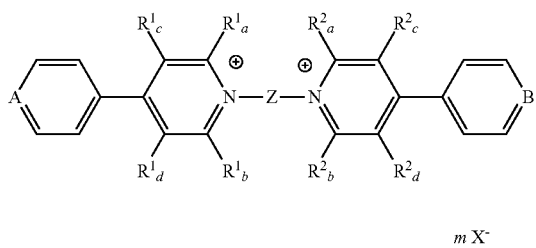

wherein:

Z is phenylene

A and B are respectively selected from nitrogen and —N⁺(R$^{7a}$)—, and from nitrogen and —N(R$^{7b}$)—, wherein R$^{7a}$ and R$^{7b}$ are independently selected from:
alkyl which may be substituted by one or more groups independently selected from halogen, alkoxy, cycloalkyl, vinyl, allyl, aryl, and substituted aryl;
aryl may be substituted by one or more groups independently selected from:
halogen, cyano, nitro, alkyl, haloalkyl, arylalkyl, cycloalkyl, cycloalkylalkyl, alkenyl, alkynyl, allyl, vinyl, aryl, substituted aryl, —N(aryl)$_2$, —N(aryl)CO(aryl), —CO-aryl and —CO-substituted aryl;
—OR$^8$, —SR$^8$, —S(O)R$^8$, —S(O$_2$)R$^8$, —S(O$_2$)NR$^8$R$^9$, —NR$^8$R$^9$, —NR$^8$COR$^9$, —NR$^8$CO(aryl), —CH$_2$OR$^8$, —CH$_2$SR$^8$, —CH$_2$R$^8$, —CO—R$^8$ and —CO$_2$R$^8$ wherein R$^8$ and R$^9$ are independently selected from H, alkyl, haloalkyl, arylalkyl, cycloalkyl, and cycloalkylalkyl;
V—W—R$^{12}$ wherein:
V is selected from oxygen, —N(R$^8$)—, sulfur, —S(O)— and S(O$_2$)— wherein R$^8$ is as defined above;
W is alkylene, which may be substituted by one or more groups independently selected from halogen and alkoxy; and
R$^{12}$ is selected from —OR$^8$, —NR$^8$(alkyl) and —SR$^8$ wherein R$^8$ is as defined above; and
—OC(O)—R$^{13}$ wherein R$^{13}$ is selected from alkyl, haloalkyl, alkenyl, —W—R$^{12}$, and aryl group which may be substituted by 1 to 4 groups selected from halogen, —R$^8$, —OR$^8$, —SR$^8$, —NR$^8$R$^9$, —NR$^{10}$R$^{11}$, —CO—R$^8$, —C(O)OR$^8$ wherein R$^8$, R$^9$, R$^{10}$, R$^{11}$, R$^2$ and W are as defined above;
R$^1_a$, R$^1_b$, R$^1_d$, R$^2_a$, R$^2_b$, R$^2_c$ and R$^2_d$ are selected from H, aryl, and substituted aryl, provided that at least one of R$^1_a$, R$^1_b$, R$^1_c$, R$^1_d$, R$^2_a$, R$^2_b$, R$^2_c$ and R$^2_d$ is not H;
X$^-$ is a counterion selected from halide, tetrafluoroborate, tetraphenylborate, hexafluorophosphate, nitrate, methanesulfonate, trifluoromethane sulfonate, toluene sulfonate, hexachloroantimonate, bis(trifluoromethanesulfonyl)imide, perchlorate, acetate and sulfate; and
m is 2 if A and B are nitrogen, 3 if one of A and B is nitrogen and the other is —N⁺(R$^{7a}$)— or —N⁺(R$^{7b}$)—, and 4 if both A and B are —N⁺(R$^{7a}$)— or N⁺(R$^{7b}$)—.

2. The compound according to claim 1, wherein A and B are respectively selected from nitrogen and —N⁺(R$^{7a}$)—, and from nitrogen and —N⁺(R$^{7b}$)—, wherein R$^{7a}$ and R$^{7b}$ are independently selected from C$_6$-C$_8$ alkyl, phenyl and naphthyl which may be both substituted by one or more substituents selected from halogen, cyano, nitro, hydroxy, C$_1$-C$_4$ alkyl, C$_1$-C$_4$ haloalkyl, C$_1$-C$_4$ alkoxy, C$_1$-C$_4$ haloalkoxy, C$_1$-C$_4$ alkylthio, C$_1$-C$_4$ haloalkylthio, C$_3$-C$_7$ cycloalkyl, and (C$_3$-C$_7$ cycloalkyl)C$_1$-C$_4$ alkyl.

3. The compound according to claim 1, wherein said compound is represented by formula (I-3):

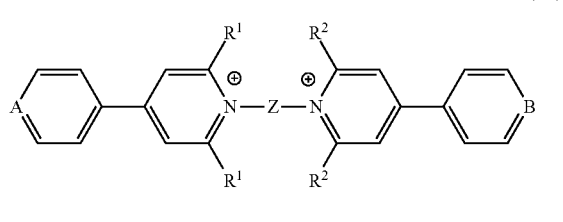

wherein Z, A, B, X$^-$, m and R$^1$ and R$^2$ are as defined in claims 1 and 2.

4. The compound according to claim 3, wherein R$^1$ and R$^2$ are each independently selected from phenyl, m-methylphenyl and p-trifluoromethylphenyl.

5. The compound according to claim 1, wherein said compound is selected from:

UNITED STATES PATENT AND TRADEMARK OFFICE
CERTIFICATE OF CORRECTION

PATENT NO. : 10,179,768 B2  
APPLICATION NO. : 15/022841  
DATED : January 15, 2019  
INVENTOR(S) : Stuart Aiken et al.

Page 1 of 1

It is certified that error appears in the above-identified patent and that said Letters Patent is hereby corrected as shown below:

In the Claims

Claim 1, Column 35, Line 39:
Delete "-N($R^{7b}$)-" and replace with -- -N+($R^{7b}$)- --

Claim 1, Column 35, Line 53:
Delete "-$CH_2OR^8$" and replace with -- -$NR^8$aryl, -$CH_2OR^8$ --

Claim 1, Column 35, Line 66:
Delete "-OC(O)-$R^3$" and replace with -- -OC(O)-$R^{13}$ --

Claim 1, Column 36, Line 24:
Insert -- $R^1_c$ -- before "$R^1_d$"

Signed and Sealed this  
Eighteenth Day of June, 2019

Andrei Iancu  
*Director of the United States Patent and Trademark Office*